United States Patent
Axelsson et al.

(10) Patent No.: US 9,999,693 B2
(45) Date of Patent: Jun. 19, 2018

(54) NANOSTRUCTURES AND APPLICATIONS THEREOF

(71) Applicant: SPAGO NANOMEDICAL AB, Lund (SE)

(72) Inventors: Oskar Axelsson, Höör (SE); Sania Bäckström, Malmö (SE); Rodrigo Petoral, Jr., Lund (SE)

(73) Assignee: SPAGO NANOMEDICAL AB, Lund (SE)

( * ) Notice: Subject to any disclaimer, the term of this patent is extended or adjusted under 35 U.S.C. 154(b) by 0 days. days.

(21) Appl. No.: 15/129,229

(22) PCT Filed: Mar. 27, 2015

(86) PCT No.: PCT/EP2015/056739
§ 371 (c)(1),
(2) Date: Sep. 26, 2016

(87) PCT Pub. No.: WO2015/144891
PCT Pub. Date: Oct. 1, 2015

(65) Prior Publication Data
US 2017/0106105 A1    Apr. 20, 2017

(30) Foreign Application Priority Data
Mar. 28, 2014 (EP) .................................... 14162399

(51) Int. Cl.
C08G 77/30    (2006.01)
A61K 51/06    (2006.01)
A61K 51/12    (2006.01)

(52) U.S. Cl.
CPC ........ *A61K 51/065* (2013.01); *A61K 51/1251* (2013.01); *C08G 77/30* (2013.01)

(58) Field of Classification Search
None
See application file for complete search history.

(56) References Cited

U.S. PATENT DOCUMENTS 8,592,036 B2    11/2013  Ludwig et al.
2004/0258614 A1  12/2004  Line et al.
(Continued)

FOREIGN PATENT DOCUMENTS

EP    1500670 A1    1/2005
EP    2572736 A1    3/2013
(Continued)

OTHER PUBLICATIONS

Hong et al. "Molecular imaging and therapy of cancer with radiolabeled nanoparticles" Nano Today, 2009, 4, 399-413 (Year: 2009).*

(Continued)

*Primary Examiner* — Robert S Loewe
(74) *Attorney, Agent, or Firm* — Harness, Dickey and Pierce, P.L.C.

(57) ABSTRACT

Disclosed herein are globular nanostructures having a hydrodynamic diameter ($D_h$) of 8-100 nm comprising a central part and a peripheral part, wherein said central part has a calculated diameter ($D_c$) of 6-90 nm and said peripheral part has an estimated thickness ($T_p$) so that $D_h = D_c + 2T_p$, wherein said central part comprises: (i) a crosslinked polymeric framework comprising monomer residues wherein at least 30% by number of the monomer residues have crosslinked thereby forming the crosslinked polymeric framework and/or (ii) a branched polymeric framework comprising monomer residues wherein the number of branch points is at least 30% of the number of monomer residues, wherein said central part comprises chelating groups of which at least 4 allow chelation of at least one multiply charged cation, wherein said chelating groups are independently selected from the group consisting of —$COOR^1$, —$P=O(OR^1)(OR^2)$, and —$S(=O)_2OR^1$, wherein $R^1$ and $R^2$ are independently selected from the group consisting of a negative (Continued)

charge, H, and lower alkyls, and wherein said peripheral part comprises a synthetic polymer material covalently attached to the central part, wherein the synthetic polymer material is hydrophilic and bioinert, and electrically neutral or zwitterionic. Also disclosed are compositions comprising such nanoparticles, and optionally also a radionuclide, use of such compositions, kits containing such compositions and methods for obtaining such compositions.

13 Claims, 7 Drawing Sheets

(56) References Cited

U.S. PATENT DOCUMENTS

| | | | |
|---|---|---|---|
| 2008/0095699 A1 | 4/2008 | Zheng et al. | |
| 2010/0297007 A1* | 11/2010 | Lanza | A61K 9/1075 424/1.65 |
| 2012/0082728 A1* | 4/2012 | Schneider | B82Y 5/00 424/491 |
| 2014/0004048 A1 | 1/2014 | Vinogradov et al. | |
| 2014/0243664 A1* | 8/2014 | El-Sayed | A61K 49/22 600/431 |

FOREIGN PATENT DOCUMENTS

| | | | | |
|---|---|---|---|---|
| WO | WO-2003/089106 A2 | 10/2003 | | |
| WO | WO-2004/040972 A2 | 5/2004 | | |
| WO | WO-2009/115579 A1 | 9/2009 | | |
| WO | WO-2009110939 A2 | 9/2009 | | |
| WO | WO-2009/124388 A1 | 10/2009 | | |
| WO | WO-2011/078803 A1 | 6/2011 | | |
| WO | WO-2013041623 A1 * | 3/2013 | | A61K 49/12 |

OTHER PUBLICATIONS

Hruby et al. "Thermoresponsive, Hydrolytically Degradable Polymer Micelles Intended for Radionuclide Delivery" Macromol. Biosci. 2009, 9, 1016-1027. (Year: 2009).*

Thaddeus J. Wadas et al: "Coordinating Radiometals of Copper, Gallium, Indium, Yttrium, and Zirconium for PET and SPECT Imaging of Disease", Chemical Reviews, vol. 110, No. 5, May 12, 2010 (May 12, 2010), pp. 2858-2902.

Coleman, R. (1991) "Single Photon Emission Computed Tomography and Positron Emission Tomography in Cancer Imaging" Cancer 67:1261-1270.

Fessenden, R. et al. (1980) "Trends in Organosilicon Biological Research" Advances in Organometallic Chemistry, vol. 18: 275-299.

Fried, J. (1995) "Polymer Science and Technology" Prentice Hall.

Hanssen, R. et al. (2004) "The Dynamic Status Quo of Polyhedral Silsesquioxane Coordination Chemistry" Eur. J. Inorg Chem. 675-683.

Hermanson, G. (2008) 2nd Edition "Bioconjugate Techniques" Elsevier.

Luk, B.et al. (2012) "Lipid- and Polymer-Based Nanostructures for Cancer Theranostics" Theranostics 2(12): 117-1126.

Malam, Y. et al.(2009) "Liposomes and nanoparticles: nanosized vehicles for drug delivery in cancer" Trends Pharmacol Sci 30(11): 593-599.

Milenic, D. et al. (2004) "Antibody-Targeted Radiation Cancer Therapy" Nature Reviews Drug Discovery, vol. 3, 488-498.

Peleshanko, S. et al. (2008) "The architectures and surface behavior of highly branched molecules" Progress in Polymer Science 33:523-580.

Sharkey, R. et al. (2011) "Cancer radioimmunotherapy" Immunotherapy 3(3):349-370.

Shirley, M. et al. (2014) "Radium-223 Dichloride: A Review of Its Use in Patients with Castration-Resistant Prostate Cancer with Symptomatic Bone Metastases" Drugs 74:579-586.

Taurin, S. et al. (2012) "Anticancer nanomedicine and tumor vascular permeability; Where is the missing link?" Journal of Controlled Release 164:265-275.

Ting, G. et al. (2010) "Nanotargeted Radionuclides for Cancer Nuclear Imaging and Internal Radiotherapy" Journal of Biomedicine and Biotechnology, 2010: 1-7.

Venditto, V. et al.(2013) "Cancer nanomedicines: So many papers and so few drugs!" Advanced Drug Delivery Reviews 65:80-88.

Venturoil, D. et al. (2005) "Ficoll and dextran vs. globular proteins as probes for testing glomerular permselectivity: effects of molecular size, shape, charge, and deformability" American Journal of Physiology 288: F605-F613.

Wen, S. et al. (2013) "Surface Modification and PEGylation of Branched Polyethyleneimine for Improved Biocompatibility" Journal of Applied Polymer Science, 3807-3813.

Öcal, H. et al. (2014) "5-Fluorouracil-loaded PLA/PLGA PEG-PPG-PEG polymeric nanoparticles: formulation, in vitro characterization and cell culture studies" Drug Development and Industrial Pharmacy 40(4): 560-567.

* cited by examiner

NANOSTRUCTURES AND APPLICATIONS THEREOF

PRIORITY STATEMENT

This patent application is a U.S. national stage filing under 35 U.S.C. § 371 of International Application No. PCT/EP2015/056739 filed on 27 Mar. 2015, which claims priority to European Patent Application No. 14162399.1 filed on 28 Mar. 2014. The entire disclosures of each of the above recited applications are incorporated herein by reference.

TECHNICAL FIELD OF THE INVENTION

The present invention relates to bioinert chelating polymeric nanostructures with applications in systemic radiotherapy and cancer imaging.

BACKGROUND

The gold standard for cancer treatment is surgery. In cases where surgery alone is not curative, multimodality regimens including chemotherapy and radiation treatment are used. About half of all cancer patients today are treated with radiotherapy, either alone or in combination with other treatments. Radiation delivered as external beams offers a relatively simple and practical approach to causing radiation damage to the tumor. Although the intensity, location and timing for external radiation can be well controlled and modulated, disadvantages associated with this technique include the destruction of normal tissue in the path of the beam as well as damage to tissues surrounding the tumor. The risk of damaging surrounding healthy tissue speaks against external radiotherapy to deeply situated tumors and tumors situated next to vital organs. Furthermore, high radiation doses are frequently required to penetrate the tissue. Moreover, in order to be efficient, external radiotherapy often requires the patients to submit themselves to daily hospital visits over extended periods of time.

Systemic radiotherapy, which internally delivers radioactive substances to the tumor, offers solutions to many of the above mentioned disadvantages connected with external radiotherapy.

The most commonly used radionuclides for systemic radiotherapy in clinics today are beta-emitting particles. Beta-emitters with energies between 0.1-2.2 MeV are ideal for the treatment of small to large clusters of tumor cells (Milenic et al., Nature Reviews Drug Discovery, 2004, 3). The maximum tissue penetration range (1-10 mm) and cross-fire effects, i.e. the ability to kill cells indirectly along a longer path length, of beta-particles of such energies thus allows for the targeting of tumor cells in close proximity to neovasculature. Radionuclides such as $^{131}$I are used alone, as in the treatment of thyroid cancers, or conjugated with monoclonal antibodies or peptides to allow for tumor-targeting radioimmunotherapy. Ibritumomab tiuexan with $^{90}$Y (Zevalin®) and tositumomab coupled with $^{131}$I (Bexxar®) are two examples of approved radioimmunotherapy regimens both targeting B lymphocytes to treat B-cell non-Hodgkin lymphoma (Sharkey and Goldenberg, Immunotherapy, 2011, 3:3).

Clinical use of alpha-emitters is less common, but some show clinical potential. As an example, the alpha-emitter $^{223}$Ra (Xofigo®) has recently been FDA-approved for treatment of metastatic bone cancer (Shirley and McCormack, Drugs, 2014).

Recent advances in nanotechnology have led to the development of novel nanocarriers designed for cancer detection and screening, in vivo molecular and cellular imaging as well as the delivery of therapeutics. However, despite a large number of publications covering nanosized carriers for cancer therapeutics, relatively few have reached clinical trials, and only a handful are approved by the FDA (Taurin et al., J. Controlled release 2012, 164). Among nanostructures used as drug vehicles, liposomes are most established. Doxil® and DaunoXome®, two liposomal formulations of doxorubicin and daunorubicin respectively, were approved in 1995 and 1996 respectively. Compared to liposomes, polymeric drug carriers should be advantageous as drug carriers due to higher stability, sharper size distribution and more controllable physicochemical and drug release properties. In the list of polymeric materials approved by the FDA for cancer therapeutics, only pegylated proteins e.g. Oncaspar® and Zinostatin Stimalmer® (SMANCS), and Abraxane®, which is paclitaxel bound to albumin, are mentioned (Venditto and Szoka Jr., Adv Drug Rev. 2013, 65:1).

Loading nanocarriers designed for systemic radiotherapy with radionuclides suitable for medical imaging in addition to radionuclides suited for radiotherapy, or a radionuclide suited for both, brings forward a possibility for a theranostic application of nanocarriers in cancer care. Gamma emitters with energies ranging from approximately 75 to 360 keV are suited for gamma detectors and single photon emission computed tomography (SPECT), whereas high-energy positron-emitting radionuclides which yield gamma photons of 511 keV can be applied for positron emission tomography (PET) (Coleman, Cancer. 1991, 67:4). Efforts to create theranostic nanocarriers are reviewed in Luk et al., Theranostics, 2012, 2:12.

The present invention relates to globular, bioinert, chelating polymeric nanostructures with applications in radioisotope therapy and cancer diagnostics. The following literature examples are examples of relevant background publications, which in no way are to be construed as being within the scope of the current invention.

International publication WO 2009/124388 discloses a hydrogel system having a covalently crosslinked polymer matrix core, with some features in common with the central part of the current invention. However, it describes microbeads much larger than the nanostructures of the current invention, it thus falls outside our scope.

United States Patent Application 20140004048 describes a nanostructure which in conformity with the nanostructure presented in the current disclosure in some embodiments has a central and a peripheral part, but where the peripheral part comprises well defined dendritic structures rather than the random polymers which are advantageous for the present invention.

Materials with a core-shell structure designed for carrying e.g. chemotherapeutic agents, are generally not suited for the application of the current invention e.g. U.S. Pat. No. 8,592,036 which describe nano-constructs where the central part is biodegradable and hence outside the scope of the current invention.

European Patent Application EP1500670 describes a material which in certain embodiments has features in common with the current invention but where the degree of crosslinking is low and is hence outside the scope of the current invention.

Structures in WO 2003/089106A2 fall outside the scope of the current invention, as it covers materials where the central part of the structures, in some embodiments is branched. They also have a peripheral part, but the structures lack the feature of carrying chelating groups which is central for the current invention.

Moreover, several approaches described in the literature (e.g. Ocal H., et al., Drug Development and Industrial Pharmacy, 2014, 40:4; WO/2009115579; WO 2011/078803), involve biodegradable materials which allow for fast or slow release of the carried therapeutic agent. The structure presented in the current invention is bioinert, as biodegradability would cause undesirable and uncontrolled loss of the radioactive isotope from the nanostructure and hence cause radiation damage in important organs.

A number of nanoparticle-based radiation delivery agents are known in the art (e.g. Ting G. et al., Journal of Biomedicine and Biotechnology, 2010; Luk et al., Theranostics. 2012, 2:12). Several approaches involve actively targeted materials, in which the nanostructure is linked to a bioconjugate, e.g. an antibody or a peptide which allows for tumor-targeting delivery through molecular interaction. Actively targeted approaches are often limited by insufficient delivery of therapeutic agents to tumor sites due to relatively low and heterogeneous expression of tumor specific targets. Moreover, expression of target proteins on non-tumorigenic cells could lead to systemic toxicity. Sometimes the introduction of the bioconjugate leads to increased liver uptake.

Many of the approaches to radiotherapy involving nanocarriers suggested in the literature, e.g. nanocarriers based on liposomes (Malam et al., Trends Pharmacol Sci. 2009, 30:11) suffer from the drawback that the radioactive isotope has to be incorporated in or encapsulated by or covalently bound to the nanocarrier by one or more chemical steps. This is usually not desirable since normally the radioisotope would be supplied by a third party and incorporated in the nanocarrier at a hospital with limited laboratory facilities. The materials of the current invention overcome this by being able to rapidly bind the isotopes when supplied in a multivalent cationic form, more specifically each radioisotope ion having a charge of plus two, three, or four. United States Patent Application 20040258614 discloses a material in which the radioisotope is covalently bound to the carrier. In the current invention the radioisotope is selected so that it can be bound by electrostatic interactions with the nanocarrier as opposed to being covalently bound which has the advantage of making the preparation of the therapeutic agent simpler and more user-friendly. Thus, the material in the above-mentioned patent application is outside the scope of the present invention.

Also, many of the approaches to radioisotope therapy involving alleged nanocarriers mentioned in the literature suffer from the drawback that the nanocarrier is not really a nanocarrier as it is larger than 100 nm and due to its large size suffers from the drawback of not delivering the radioisotope to the tumor tissue in an effective way. The materials disclosed in the current invention focus on nanocarriers or nanomaterials that are above the threshold where they would be excreted through the kidneys and hence either cause damage and/or be lost from the body while at the same time being small enough (below 100 nm diameter) to be able to leak out through defective capillaries and diffuse through the intracellular matrix and deliver the radioactivity to the tumor cells. WO 2004/040972 is one example of a carrier that is larger than 100 nm, and thus lies outside the scope of the current invention. Furthermore, the rationale for nanosized materials being suitable as tumor-targeting radiation carriers is related to the enhanced permeation and retention (EPR) effect. The EPR effect is based on the fact that whereas the capillaries of healthy tissues are virtually impermeable to molecules larger than 3-4 nm, capillaries of fast-growing tumor tissue are much leakier. In addition, solid tumors tend to lack functional lymphatics. Combined, these features limit the removal of extravasated nanomaterials from most solid tumors. Because EPR-mediated drug targeting exclusively relies on the pathological properties of the target tissue, that is, enhanced leakiness and poor lymphatic drainage, it is generally referred to as passive tumor targeting.

Although in no way certain or limiting, it is conceivable that the EPR effect is the basis of the favorable tumor delivery properties of the materials of the current invention.

SUMMARY OF THE INVENTION

Some advantages with the nanostructures disclosed herein over prior art include a "theranostic" application in which the nanostructure can be used to diagnose cancer, deliver tumor-targeted therapy as well as monitor the response to therapy. A passive targeted approach as utilized by the current invention, enables for treatment and detection of larger tumor masses as well as smaller tumor loads and metastasized disease. The disclosed nanostructure enables for a higher effective dose to be delivered to the tumor and thus lowers the radiation dose as well as limits the general toxicity and damage to surrounding tissue as frequently seen with systemic chemotherapy and external beam radiotherapy. The design of the current invention allows for simplified management and handling at the hospital and thus improves utility in clinical practice.

The first major aspect of the current invention relates to a globular nanostructure having a hydrodynamic diameter ($D_h$) of 8-100 nm comprising a central part and a peripheral part, wherein said central part has a calculated diameter ($D_c$) of 6-90 nm and said peripheral part has an estimated thickness ($T_p$) so that $D_h=D_c+2T_p$, wherein said central part comprises:

(i) a crosslinked polymeric framework comprising monomer residues wherein at least 30% by number of the monomer residues have crosslinked thereby forming the crosslinked polymeric framework and/or (ii) a branched polymeric framework comprising monomer residues wherein the number of branch points is at least 30% of the number of monomer residues, wherein said central part comprises chelating groups of which at least 4 allow chelation of at least one multiply charged cation, wherein said chelating groups are independently selected from the group consisting of —COOR$^1$, —P=O(OR$^1$)(OR$^2$), and —S(=O)$_2$OR$^1$, wherein R$^1$ and R$^2$ are independently selected from the group consisting of a negative charge, H, lower alkyls, and aryl and wherein said peripheral part comprises a synthetic polymer material covalently attached to the central part, wherein the synthetic polymer material is hydrophilic and bioinert, and electrically neutral or zwitterionic.

The second major aspect of the current invention is a process to produce said nanostructures. In its broadest sense it first involves the formation or acquisition of globular, nanosized polymer entities (001), later ending up comprising said central part of said nanostructures, and in no particular order followed by a step (002), which may sometimes be included in the first step (003) when said monomers already carries chelating groups or precursors of said chelating groups, introducing a multitude of chelating groups, and in no particular order, followed by a step (004) where the product of the first step(s) is contacted precursors to said peripheral apart.

The third major aspect of the current invention relates to compositions wherein the nanostructures according to the first major aspect, or the nanostructures obtained in accordance with the second major aspect are combined with radionuclides, particularly radionuclides for therapeutic and/or diagnostic applications.

The fourth major aspect of the present invention relates to methods of obtaining the composition in accordance with the third major aspect of the invention.

The fifth major aspect of the current invention relates to the use of a composition comprising a plurality of said nanostructures comprising a radionuclide for imaging and/or radiotherapy as an imaging and/or radiotherapeutic agent for diagnostic and/or radiotherapeutic procedures. The composition comprising a plurality of said nanostructures comprising a radionuclide for imaging and/or therapy can be used to diagnose, deliver radiotherapy as well as monitor the response to radiotherapy.

The sixth major aspect of the present invention relates to a kit comprising nanostructures according to the first major aspect or nanostructures obtained in accordance with the second major aspect, and in some embodiments also a radionuclide for imaging and/or radiotherapy.

Definitions of Terms

The term "nanostructure" as used herein relates to an entity with a total size in the nanorange, i.e. up to 100 nm. As used herein the term excludes the structures often referred to as "core-shell nanoparticles" or just "nanoparticles" which usually have an inorganic core and an organic coating.

The term "globular" as used herein is meant to describe a shape such that the minor axis is no less than half of the major axis, i.e. the longest axis through the center (point of weight) of the structure is no more than twice the length of the shortest axis through the same point. For an explanatory illustration, not limiting this definition, see FIG. 1.

The term "globular nanostructure" as used herein relates to a nanostructure as discussed above having an essentially globular form or shape. This means that shapes such as flakes, rods, tubes, toroids, chains and ribbons are excluded.

The term "hydrodynamic diameter" as used herein refers to the diameter of the hypothetical hard sphere that diffuses at the same speed as the particle, i.e. the diameter of the equivalent hard sphere as calculated from the diffusion coefficient, according to the Stokes-Einstein equation. The term is also known as "Stokes diameter" or "Stokes-Einstein diameter". Hydration and shape are included in the behavior of the sphere. The diffusion coefficient is in turn calculated from e.g. the time dependent light scattering data obtained by the Dynamic Light Scattering (DLS) technique. Other technical methods to measure the diffusion coefficient of nanostructures are known to one skilled in the art and may be used instead. In those cases, measurements need to be referenced to the DLS-measurement. As a comparison, bovine serum albumin is measured to have a hydrodynamic diameter of 6.5 nm by DLS in aqueous saline at pH 7 and room temperature. Depending on whether the number average, volume average, or scattered intensity average is used, the calculated values may be somewhat different. The volume average is generally the most useful since it shows which particle size the bulk of the material has. The average diameters referred to in this text refers to volume averages as measured in aqueous saline at pH 7 and room temperature.

The term "DLS" as used herein is an acronym for Dynamic Light Scattering, a particle sizing method, and may also be referred to as Photon Correlation Spectroscopy or Quasi-Elastic Light Scattering. The DLS sizes given as stated in the text and in the claims, if nothing else is specified, refers to the position of the maximum of the volume average peak for a sample measured at 25° C. in neutral aqueous solution with an ionic strength corresponding to 150 mM NaCl, also called saline.

The term "calculated diameter" refers to a diameter like that of the central part of the current invention which cannot usually be measured after assembly of the nanostructure. It is calculated in ways obvious to one skilled in the art from measureable properties like hydrodynamic diameter, density and chemical composition. Alternatively, calculations can be made from knowledge of the size of the precursor to the central part or by building molecular models e.g. computer models of said nanostructures and calculating their contributions to the overall diameter. The diameter of said central part is to be construed as an estimated or calculated average diameter over the whole interface between said central part and said peripheral part.

The term "calculated thickness" refers to a thickness like that of the peripheral part of the current invention which cannot usually be measured after assembly of the nanostructure. It is calculated in ways obvious to one skilled in the art from measureable properties like hydrodynamic diameter, density and chemical composition. Alternatively, calculations can be made from knowledge of the size of the precursor to the peripheral part, or by building molecular models e.g. computer models of said nanostructures and calculating their contributions to the overall diameter. The thickness of said peripheral part is to be construed as an estimated or calculated average thickness over the whole interface between said central part and said peripheral part.

A "monomer" is a molecule that may bind covalently to other molecules of the same kind, (and optionally, other kinds) to form a polymer i.e. a macromolecule composed of several monomer residues. The term "monomer residue" refers to the atoms derived from one monomer unit as incorporated into the larger polymer.

A "crosslink" refers to a link between two different chains in a polymer. It is usually formed by the reaction of multifunctional monomers (i.e. crosslinkers) added when forming the polymer. Crosslinks may also be introduced e.g. by radiation treatment, chemical means, or heat.

The term "crosslinked" refers to a structure formed after the formation of at least one crosslink.

A "branch point" is a position in a tree-like polymer where a polymer chain branches to two or more branches.

The term "polymeric framework" as used herein relates to a covalently bound group of atoms forming either a multi-branched tree like structure or a network structure with multiple crosslinks. Such polymeric frameworks are formed from the linking of suitable monomers and/or oligomers (i.e. a molecular complex consisting of a few monomer residues) via covalent bonds. Typical monomers can be found in textbooks of polymer chemistry such as J. R. Fried, "Polymer Science and Technology" Prentice Hall 1995. Some examples of monomers are styrene, propylene, ethylene, tetrafluoroethylene, trifluoroethylene, difluoroethylene, methyl acrylate, ethyl acrylate, hydroxyethyl acrylate, acrylamide, methyl methacrylate, ethyl methacrylate, hydroxyethyl methacrylate, $H_2N-(CH_2)_p-COOH$, where p is 1-10, 3-aminobenzoic acid, 4-aminobenzoic acid, N-vinyl pyrolidone and silicone precursors like $(CH_3COO)_2Si(CH_3)_2$. Some examples of polymer frameworks are formed from matching pairs of monomers like terephtalic acid+1,4 diamino benzene, terephtalic acid+ethylene glycol, and HCOO—$(CH_2)_p$COOH+$H_2$N—$(CH_2)_q$—$NH_2$, where p and q independently are 1-10. Oligomers with 2-10 monomer units linked can be used as precursors. Some examples of oligomers different from linked groups of the above monomers are cyclic or poly-cyclic silanes such as hexamethylcyclotrisiloxane, 2,4,6,8-tetramethylcyclotetrasiloxane, and decamethylcyclopentasiloxane. Typical crosslinkers can be found in textbooks of polymer chemistry such as J. R. Fried, "Polymer Science and Technology" Prentice Hall 1995. Some examples of crosslinkers are N,N'-methylenebis(acrylamide), O,O'-methylenebis(acrylic acid), epichlorohydrin, divinylbenzene, 1,3-divinyltetramethyldisiloxane, 1,3-phenylenediisocyanate, 3,3"-biphenyltetracarboxylic acid dianhydride, 1,4-butanedioldivinylether, tetraethoxysilane, oligosilicates such as metasilicate, or silsequioxanes, organosilanes such as bis(triethoxysilyl)methane, bis(triethoxysilyl)ethane, bis(triethoxysilyl)propane, bis(triethoxysilyl)butane, methyl triethoxysilane, ethyl triethoxysilane, and propyl triethoxysilane.

The polymeric framework constitutes the skeleton of the central part of the nanostructure. The skilled person realizes that the random nature of the polymerization process causes the materials to be mixtures of many similar but in most cases not identical branching patterns, crosslink positions and molecular weights.

The term "branched" in the context of the polymeric framework of the central part according to the present invention refers to polymeric materials that are compositionally not very far from conventional dendrimers but show a less regular architecture and often a lower degree of branching. The molecules have a fractal structure with a multitude of branches. They are created in one-pot synthesis without the lengthy stages of stepwise reaction and purification necessary with traditional dendrimers (Peleshanko, S. and Tsukruk, V. V., Prog. Polym. Sci. 2008, 33:523). The term includes both so called multiply branched polymeric frameworks and so called hyperbranched polymeric frameworks. However a criterion according to the present invention is that the branched polymeric frameworks comprise monomer residues wherein the number of branch points is at least 30% of the number of monomer residues.

The term "chelating group" refers to a chemical group with the ability to successfully compete with water in electrostatic binding of a positively charged ion. A single chelating group does not bind very strongly but if several of them surround a positively charged ion, a synergistic strengthening of the binding occurs. This is called chelation.

The expression "arranged in a fashion that allows chelation" means that a number of chelating groups as defined above are arranged so that synergistic strengthening of the binding of a positively charged ion can occur. This can be obtained by either statistical means; when a large number of chelating groups are incorporated in a random polymer at such a density that at least a few of them find themselves in proximity so that they can bind the same positively charged ion; or by incorporating a preformed unit where the chelating groups are already sitting in close proximity. An example of the latter is the well-known chelator DOTA.

The term "covalently attached", "covalently linked" and "covalently bound" as used herein are synonymous, and the meaning thereof is well known to the skilled person.

The term "independently selected" as used herein means that each of the different constituents mentioned before the term is selected from the group following after the term independently or separately from the selection of the other mentioned constituents.

The term "geminal bisphosphonate group" refers to two phosphonate groups separated by one carbon atom, i.e. the phosphonate groups are bound to the same carbon atom. Compounds comprising such a geminal bisphosphonate group are often referred to as 1,1-bisphosphonates (or 1,1-diphosphonates). The phosphonate groups in the geminal bisphosphonate group may be substituted. In some embodiments the phosphonate groups each have the formula —P=O($OR^1$)($OR^2$) wherein $R^1$ and $R^2$ are independently selected from the group consisting of a negative charge, H, lower alkyls and aryl.

The term "radionuclide" refers to an unstable form of a chemical element that decays radioactively, resulting in the emission of α, β and/or γ radiation.

As used herein, the expression "radionuclides for imaging and/or radiotherapy" refers to actinium-225 ($^{225}$Ac); copper-62 ($^{62}$Cu); copper-64 ($^{64}$Cu); copper-67 ($^{67}$Cu); gallium-67 ($^{67}$Ga); gallium-68 ($^{68}$Ga); holmium-166 ($^{166}$Ho); indium-111 ($^{111}$In); lead-212 ($^{212}$Pb); lutetium-177 ($^{177}$Lu); radium-223 ($^{223}$Ra); rhenium-186 ($^{186}$Re); rhenium-188 ($^{188}$Re); rubidium-82 ($^{82}$Rb); samarium-153 ($^{153}$Sm); strontium-89 ($^{89}$Sr); technetium-99m ($^{99m}$Tc$^{3+}$); thallium-201 ($^{201}$Tl); thorium-227 ($^{227}$Th); yttrium-86 ($^{86}$Y); yttrium-90 ($^{90}$Y); and zirconium-89 ($^{89}$Zr). The expression "a radionuclide for imaging and/or radiotherapy" also encompasses combinations of two or more of the above mentioned radionuclides.

As used herein, the expression "radionuclides for imaging" refers to copper-62 ($^{62}$Cu); copper-67 ($^{67}$Cu); gallium-67 ($^{67}$Ga); gallium-68 ($^{68}$Ga); indium-111 ($^{111}$In); lutetium-177 ($^{177}$Lu); rhenium-186 ($^{186}$Re); rubidium-82 ($^{82}$Rb): technetium-99m ($^{99m}$Tc$^{3+}$); Thallium-201 ($^{201}$Tl); yttrium-86 ($^{86}$Y) and zirconium-89 ($^{89}$Zr). The expression "a radionuclide for imaging" also encompasses combinations of two or more of the above mentioned radionuclides.

As used herein, the expression "radionuclides for PET imaging" refers to copper-62 ($^{62}$Cu); gallium-68 ($^{68}$Ga); rubidium-82 ($^{82}$Rb); yttrium-86 ($^{86}$Y) and zirconium-89 ($^{89}$Zr). The expression "a radionuclide for PET imaging" also encompasses combinations of two or more of the above mentioned radionuclides.

As used herein, the expression "radionuclides for SPECT imaging" refers to gallium-67 ($^{67}$Ga); indium-111 ($^{111}$In); technetium-99m ($^{99m}$Tc$^{3+}$) and thallium-201 ($^{201}$Tl). The expression "a radionuclide for SPECT imaging" also encompasses combinations of two or more of the above mentioned radionuclides.

As used herein, the expression "radionuclides for radiotherapy" refers to actinium-225 ($^{225}$Ac); copper-64 ($^{64}$Cu); copper-67 ($^{67}$Cu); holmium-166 ($^{166}$Ho); lead-212 ($^{212}$Pb); lutetium-177 ($^{177}$Lu); radium-223 ($^{223}$Ra); rhenium-186 ($^{186}$Re); rhenium-188 ($^{188}$Re); samarium-153 ($^{153}$Sm); strontium-89 ($^{89}$Sr); thorium-227 ($^{227}$Th) and yttrium-90 ($^{90}$Y). The expression "a radionuclide for radiotherapy" also encompasses combinations of two or more of the above mentioned radionuclides.

As used herein, the expression "radionuclides for PET imaging and radiotherapy" refers to actinium-225 ($^{225}$Ac); copper-62 ($^{62}$Cu); copper-64 ($^{64}$Cu); copper-67 ($^{67}$Cu); gallium-68 ($^{68}$Ga); holmium-166 ($^{166}$Ho); lead-212 ($^{212}$Pb); lutetium-177 ($^{177}$Lu); radium-223 ($^{223}$Ra); rhenium-186 ($^{186}$Re); rhenium-188 ($^{188}$Re); rubidium-82 ($^{82}$Rb); samarium-153 ($^{153}$Sm); strontium-89 ($^{89}$Sr); thorium-227 ($^{227}$Th); yttrium-90 ($^{90}$Y) and zirconium-89 ($^{89}$Zr). The expression "a radionuclide for PET imaging and radiotherapy" also encompasses combinations of two or more of the above mentioned radionuclides.

As used herein, the expression "radionuclides for SPECT imaging and radiotherapy" refers to actinium-225 ($^{225}$Ac); copper-64 ($^{64}$Cu); copper-67 ($^{67}$Cu); gallium-67 ($^{67}$Ga); holmium-166 ($^{166}$Ho); indium-111 ($^{111}$In); lead-212 ($^{212}$Pb); lutetium-177 ($^{177}$Lu); radium-223 ($^{223}$Ra); rhenium-186 ($^{186}$Re); rhenium-188 ($^{188}$Re); samarium-153 ($^{153}$Sm); strontium-89 ($^{89}$Sr); technetium-99m ($^{99m}$Tc$^{3+}$); thallium-201 ($^{201}$Tl); thorium-227 ($^{227}$Th) and yttrium-90 ($^{90}$Y). The expression "a radionuclide for SPECT imaging and radiotherapy" also encompasses combinations of two or more of the above mentioned radionuclides.

The term "bioinert" as used herein refers to a material that is biocompatible, i.e. harmless to mammals and mammalian cells and at the same time stable to degradation in vivo, in a human (less than 10% degraded) for periods of one week or more.

The term "oxysilane" as used herein refers to any organic compounds with one or more oxygen atoms attached to the silicon atom. Non-limiting examples thereof are:

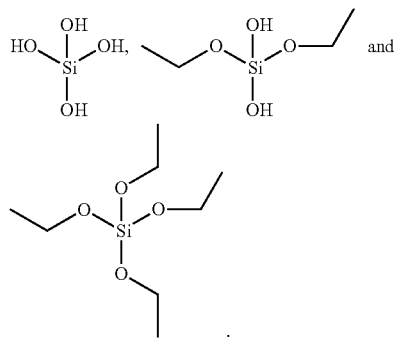

The term "organosilane" as used herein refers to organic compounds containing one or more carbon-silicon bond(s).

The terms "hydrocarbon" and "hydrocarbon chain" are used herein to denote an organic residue consisting of hydrogen and carbon. The hydrocarbon may be fully saturated or it may comprise one or more unsaturations. The hydrocarbon in accordance with the present invention may contain any number of carbon atoms between 1 and 50.

The term "alkyl" as used herein refers to a straight or branched hydrocarbon chain fully saturated (no double or triple bonds) hydrocarbon group. The alkyl group may in the present text have 1-15 carbon atoms. Typical alkyl groups include, but are in no way limited to, methyl, ethyl, propyl, isopropyl, butyl, isobutyl, tertiary butyl, pentyl, hexyl and the like.

The term "lower alkyl" as used herein refers to an alkyl having 1-8 carbon atoms.

The term "lower alcohol" as used herein refers to an alcohol having 1-8 carbon atoms.

Numerical ranges: Whenever it is used herein, unless otherwise stated, a numerical range such as "1 to 8" or "1-8" refer to each integer in the given range; e.g., "1 to 8 carbon atoms" and "1-8 carbon atoms" mean that the alkyl group may consist of 1 carbon atom, 2 carbon atoms, 3 carbon atoms, etc., up to and including 8 carbon atoms. There are, however some exceptions which are clear to the skilled persons. In particular, whenever a range is given herein for a molar ratio, such as the P/N molar ratio or the Si/P molar ratio in the nanostructures, for a diameter or size, for a pH, for a period of time, for a concentration, for an osmolality or for a temperature, the range includes also all decimal numbers falling within the range, including the upper and lower limits.

As used herein, the term "alkoxy" refers to the formula —OR wherein R is a lower alkyl, e.g. methoxy, ethoxy, n-propoxy, 1-methyl ethoxy (isopropoxy), n-butoxy, iso-butoxy, sec-butoxy, tert-butoxy, amyloxy, iso-amyloxy and the like. An alkoxy group in accordance with the present invention may be optionally substituted.

As used herein the term "aryl" refers to a carbocyclic (i.e. all carbon) ring or two or more fused rings (i.e. rings that share two adjacent carbon atoms) that have a fully delocalized pi-electron system. Examples of aryl groups include, but are not limited to, benzene, naphthalene and azulene. An aryl group in accordance with the present invention may be optionally substituted, e.g., phenoxy, naphtha-lenyloxy, azulenyloxy, anthracenyloxy, naphthalenylthio, phenylthio and the like. An aryloxy may be optionally substituted.

As used herein the term "acyl" refers to the functional group RC(=O)— with R being an organic residue.

The term "conjugate" as used herein refers to a molecular entity that is a fluorescence marker, dye, spin-label, radioactive marker, peptide, ligand to a biological receptor, chelate, enzyme inhibitor, enzyme substrate, antibody or antibody related structure. See e.g. "Bioconjugate Techniques", Greg T. Hermanson second edition, Elsevier 2008, ISBN 978-0-12-370501-3 for background on the subject.

Figure 1:
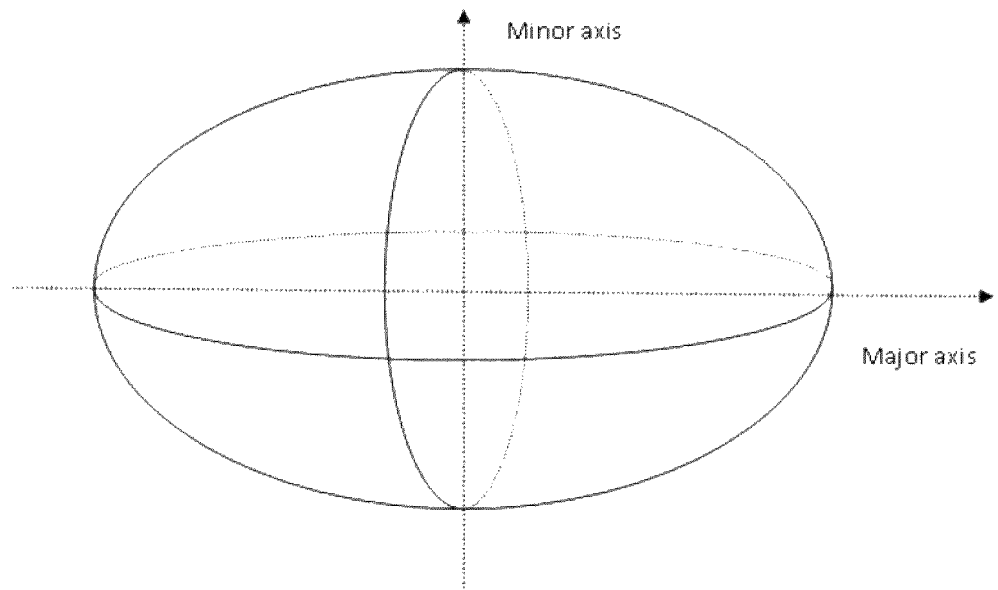
FIG. 1 is an explanatory illustration of a globular shape.

pH=2.97. pH adjusted to 9.07 with Tris buffer. GPC retention time: 13.11. Albumin retention time: 12.52. DLS $d_H$=6.56±1.78 nm. TEM image shows that nanostructures are globular and have a diameter of circa 6 nm. The dark circles in the middle of the nanostructures are attributed to uranyl-loaded core nanoparticles and the white rings are interpreted as PEG coating.

DETAILED DESCRIPTION OF THE INVENTION

A first major aspect of the current invention deals with a globular structure with a hydrodynamic diameter $D_h$, defined and measured as described above, that is in the size range of some to several nanometers, such as from 8 to 100 nm, or from 8 to 50 nm, or from 8 to 20 nm, henceforth called a nanostructure.

In some embodiments the hydrodynamic diameter of said nanostructure is between 8 and 100 nm.

In some embodiments the hydrodynamic diameter of said nanostructure is between 8 and 50 nm.

In some embodiments the hydrodynamic diameter of said nanostructure is between 8 and 20 nm.

In some embodiments of the invention, a non-limiting example being use in a composition for use as an intravenous imaging agent and/or radiotherapeutic agent, the average hydrodynamic diameter of the nanostructures is between 8 and 100 nm, or between 8 and 50 nm, or between 8 and 20 nm.

Said nanostructure is usually prepared and/or used as a plurality of said nanostructures.

Compositions comprising nanostructures of the current invention will always contain a plurality of said nanostructures and they can be characterized by statistical measures, such as, but not limited to, average diameter, molecular weight, monodispersity index, density, concentration or size measures such as the percentage passing through certain calibrated filters with nominal cut-off values for the molecular weight.

The useful range of sizes of the nanostructures of the current invention is limited from below by the physiology of the kidney of an organism such as a human. Compact structures with a hydrodynamic diameter of larger than 8 nm have negligible excretion through the kidney and hence a potential of being long-circulating in the blood stream after administration by e.g. an intravenous injection (Venturoli and Rippe, American Journal of Physiology, 2005, 288). The property of being long-circulating is advantageous for the Fourth Aspect of the current invention. The upper limit of the sizes of the nanostructures of the current invention that is useful for the present invention is set by the need to penetrate from the blood stream into tumor tissue in the body of an organism, as described below in the Fifth Aspect of the current invention. Although there is a vast literature on various micro- and nano-constructs for delivery of a payload to tumor tissue, the inventors of this invention have found that it is more advantageous to use small entities for this purpose since the diffusion resistance in tissue is high, and for entities above 100 nm diameter, it is high enough that the dose delivered locally to a tumor is too small for being useful in the Fifth Aspect of the current invention.

Although, the main thrust of the current invention is to rely on the EPR effect for selective delivery of radioisotopes to a tumor, it can be contemplated to use specific targeting of the nanostructures of the current invention if certain obstacles are overcome. The specific tumor targeting of nanocarriers today is problematic due to reasons relating to e.g. relatively low and heterogeneous expression of tumor specific targets as well as risks of systemic toxicity due to expression of target proteins on non-tumorigenic cells, the area is under rapid development. It is thus in the future conceivable that an introduction of specific tumor targeting groups into the nanostructures of the current invention could enhance both anti-tumor therapeutic activity and imaging efficacy with reduced adverse effects on healthy tissue. Such conceivable tumor-targeting groups include but are not restricted to peptides, peptoids, proteins, antibodies, DNA fragments, RNA fragments and PNA fragments.

The nanostructures of the present invention have a central part and a peripheral part attached to, and surrounding the central part. The central part and the peripheral part constitute the whole of said nanostructure. The central part is globular in its general shape but the interface between the central part and the peripheral part may be convoluted. The diameter of the central part ($D_c$) and the thickness of the peripheral part ($T_p$) can be calculated based on their relative contributions to the overall diameter as described above.

Realistically, it takes a thickness of one nanometer or more of the peripheral part surrounding the central part to render the nanostructure bioinert, and since the peripheral part is present on all sides of the central part this will contribute twice to the overall diameter, hence:

$$D_h = D_c + 2T_p \qquad \text{(Eq. 1)}$$

$$T_p = (D_h - D_c)/2 \qquad \text{(Eq. 2)}$$

Figure 2:
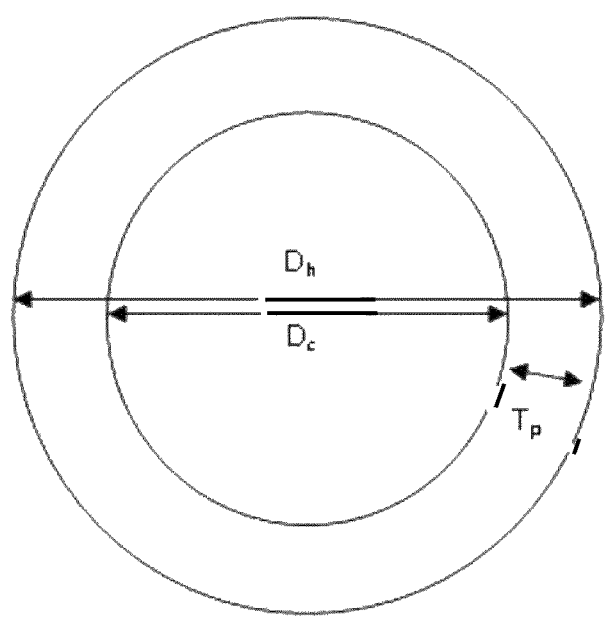
FIG. 2 is a schematic drawing of a nanostructure illustrating how the distances $D_h$, $D_c$ and $T_p$ are measured.

How $D_h$, $D_c$ and $T_p$ are measured is shown in FIG. 2.

Since the current invention deals with nanostructures with an overall hydrodynamic diameter of 8-100 nm, suitable calculated sizes of the central part are 6-90 nm or 6-45 nm or 6-15 nm, and suitable ranges of the thickness of the peripheral part ($T_p$) follow from Eq. 2.

In some embodiments said hydrodynamic diameter, $D_h$ is 8-20 nm, the calculated diameter of the central part, $D_c$, is 6-15 nm and the thickness of the peripheral part is 1-2.5 nm.

For being useful in the Fifth Aspect of this invention, the peripheral part must cover the central part to protect it from interaction with biological systems. Depending on the technical solution used to obtain this coverage, this requisite may be quantitatively explained in different ways;

For a case where said peripheral part comprises linear polymers such as A-(O—CH$_2$CH$_2$)$_m$OR$^9$ groups wherein A, m, and R$^9$ are as defined below, extending outwards from the surface of said central part, a surface density of 0.1-3 µmol/m$^2$ or 0.5-2 µmol/m$^2$ is suitable. The surface area referred to in this context is the area of the interface between said central part and said peripheral part.

In some embodiments said peripheral part comprises A-(O—CH$_2$CH$_2$)$_m$OR$^9$ covalently linked to said central part at a surface density of 0.5-2 µmol/m$^2$.

For a case where said peripheral part comprises branched polymer residues, the same range of surface density but divided by the number of branches of each individual branched polymer applies so e.g. for a peripheral part comprising polymers covalently bound to the surface, each branching at one point, henceforth called two branched polymers, a surface density of 0.05-1.5 µmol/m$^2$ or 0.25 to 1.0 µmol/m$^2$ is suitable. In a similar vein, for a peripheral part comprising n-branched polymers covalently bound to the surface, a surface density of 0.1/n-3/n µmol/m$^2$ or 0.5/n to 2.0/n µmol/m$^2$ is suitable.

For the case where said peripheral part comprises a crosslinked polymer, it is not suitable to state the surface density of said peripheral part as above but rather as a requirement that said peripheral part covers the central part and the thickness of said peripheral part in no place is less than 1 nm.

The surface density of the peripheral part is not usually directly measurable but has to be calculated from other parameters. Often it has to be calculated from data on overall hydrodynamic diameter, and the calculated size of the central part and the density of the central part or the density and composition of the peripheral part according to methods well known to one skilled in the art.

Said central part comprises a crosslinked and/or branched, polymeric framework comprising or adorned with a multitude of chelating groups. Said polymeric framework may be a homopolymer of a single monomer or a copolymer of two or more different monomers. The current invention deals with central parts comprising random polymers, as opposed to cascade polymers such as dendrimers or arborols, or macromolecules such as proteins, which all have molecularly well defined structures where essentially all molecular entities are identical. The advantage of this approach is that, although it is possible to reach the desired minimum size of 6 nm for said central part with well defined molecular entities, it is very costly and cumbersome to do so. An example would be the dendrimer PAMAM-G7 which according to the supplier has a hydrodynamic diameter of 8.1 nm, and costs approximately $7850 for a research sample of 100 mg. The typical material costs for the random polymers of the current invention are less than 1% of this. The largest dendrimer that seems to be commercially available is PAMAM-G10 and it is stated to have a hydrodynamic diameter of 13.5 nm, reaching only the lower part of the desired size range of 6-90 nm of said central part of the nanostructures in accordance with the present invention.

Polymeric frameworks in accordance with the present invention can be constructed from a large number of well known monomers as can be found in any book on polymer chemistry (e.g. Fried, "Polymer Science and Technology" Prentice Hall 1995). Some non-limiting examples are polyalkenes, polyacrylates, polymethacrylates, polyamides, polystyrenes, polydimethylsiloxanes (silicones), polyorganosilanes, polyamines such as polyethyleneimine, or carbohydrates; especially highly branched or crosslinked structures.

In some embodiments said polymeric framework is derived from polyethylene.

In some embodiments said polymeric framework is derived from polystyrene.

In some embodiments said polymeric framework is derived from polyacrylic acid.

The degree of polymerization (average number of monomer residues) of said central part is adjusted to yield products of the desired size by manipulating the process parameters as known in the art. It is less useful to describe size by degree of polymerization than hydrodynamic diameter but it is another way of conceptualizing the structures. A range is included not as limiting but rather as a reference. For example, for a polymer with a density close to 1 g/ml the typical degree of polymerization ranges from 100-2 000 000 monomers.

It is conceivable to mix two, three or several of the said polymer frameworks in any chemically compatible monomer combination, either by mixing the monomers prior to polymerization, or by grafting one polymer to another.

One established way of achieving a polymeric framework with a network structure is by introducing crosslinks via the incorporation of a fraction of bi- or poly-functional monomers in the polymerization process. The advantage of the high degree of crosslinking and/or branching used in the current invention is to render said central part rigid and less prone to swelling in media of various salt concentrations. Swelling would affect the ability of the material to diffuse in tissue and would also in many cases, such as those where the chelating groups are randomly distributed in the polymer, lead to undesirable lowering of the ability of the material to chelate said multiply charged cations. A non-limiting list of typical cross-linking agents are N,N'-methylenebis(acrylamide), epichlorohydrin, divinylbenzene, 1,3-divinyltetramethyldisiloxane, 1,3-phenylenediisocyanate, 3,3'-biphenyltetracarboxylic acid dianhydride, bis(trimethoxysilyl)methane, bis(trimethoxysilyl) ethane, and 1,4-butanedioldivinylether.

The degree of crosslinking or branching of said polymer of said central part of the current invention is unusually high for random polymers such as on average more than one crosslink per monomer i.e. >100% crosslinking or branching; or 50% crosslinking or branching; or 30% crosslinking. Even such high degrees as 300-400%, or less than but close to 600% may be contemplated for some polymeric frameworks of the current invention. It is obvious to the person skilled in the art that even if monomers with potential for crosslinking or branching are used as monomers used to produce said central part, not all of the potential will be fulfilled in practice so some residual groups with potential for crosslinking or branching will be left in the structure of said central part. In polymer literature it is often not stated whether the degree of crosslinking is the actual, achieved or the potential for crosslinking. In the current disclosure it is stated which case the inventors refer to by clearly stating "% crosslinker added" for the case of potential for crosslinking and "% crosslinking achieved" for actual measured values.

In some embodiments said central part comprises a homopolymer where there are six groups with potential for crosslinking in the monomer which corresponds to 600% of crosslinker added and between 2 and 5 of the groups actually form crosslinks corresponding to 200%-500% crosslinking achieved.

In some embodiments the percentage of crosslinker added is between 30% and 100%.

In some embodiments the degree of crosslinking achieved is between 30% and 100%.

In some embodiments the degree of branching achieved is between 30% and 100%.

In some embodiments the degree of crosslinking achieved is between 200% and 400%.

In some embodiments the percentage of crosslinker added is between 500% and 600%.

One particularly framework that may be advantageous for some embodiments of the invention is formed by the condensation polymerization of trialkoxyorganosilanes $R^{12}$—Si(OR$^{13}$)$_3$, with $R^{12}$ being H or an organic residue and $R^{13}$ independently being a lower alkyl or aryl. Such a framework has the property of being highly polar, hence compatible with water, and the degree of crosslinking can be controlled by the process parameters during production. It may be advantageous to use monomers with more than one trialkoxysilyl group present.

In some embodiments of the invention there are two alkoxysilane groups present in the monomer.

In some embodiments of the invention said alkoxysilanes are separated by 1-10 carbon atoms or 3-9 carbon atoms.

In some embodiments of the invention said alkoxysilanes are separated by 7 carbon atoms.

In some embodiments of the invention the two phosphonate groups are part of the group $R^{12}$.

In some embodiments of the invention said two silanes are separated by 7 carbon atoms and the two phosphonate groups are part of the group $R^{12}$.

In some embodiments of the invention said silanes have the generic structure:

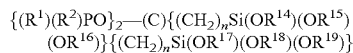

wherein
$R^1$ and $R^2$ are independently selected from the group consisting of negative charge, H, lower alkyls, and aryl and $R^{14}$, $R^{15}$, $R^{16}$, $R^{17}$, $R^{18}$, and $R^{19}$ are independently selected from the group consisting of lower alkyls and aryl; and
n=1-5.

In some embodiments said monomer residues include monomer residues having the structure $(R^3O)(R^4O)(R^5O)Si$—$(CH_2)_n$—$C(P=O(OR^1)(OR^2))_2$—$(CH_2)_n$—$Si(OR^6)(OR^7)(OR^8)$, wherein $R^3$, $R^4$, $R^5$, $R^6$, $R^7$, and $R^8$ are independently selected from the group consisting of a negative charge, H, lower alkyls and a bond to the polymeric framework, and n=1-5
and wherein said monomer residues are incorporated in said polymeric framework by means of —O—Si bonds, wherein the silicon atom is a silicon atom in the above structure.

The reactivity of the trialkoxy silanes in the above monomers towards polymerization varies with the identity of the $R^{14-19}$ groups. The inventors have found this to be a critical factor in the control of molecular size during production and found the methyl and ethyl, in particular the latter, to be suitable for yielding the structures of the present invention although it is conceivable to use any other lower alkyl group, aryl, silyl amide, acyl, silylfluoride or silylchloride.

In some embodiments of the invention $R^{14-19}$ in said monomers are ethyl groups.

There are many different ways trialkoxy silanes may link to each other via Si—O—Si bonds. Dimeric structural elements as well as linear, branched, and cyclic are known (Fessenden and Fessenden, "Trends in Organosilicon Biological Research; Advances in Organometallic Chemistry, 1980, 18). Also Silicon-oxygen cage structures of various sizes are well known from the literature (Hanssen, Eur. J. Inorg. Chem, 2004, 675) and residual alkoxy groups or free silanol groups may also be present to different degrees. Some structural elements, though in no way to be construed as limiting, that may be present in such structures are:

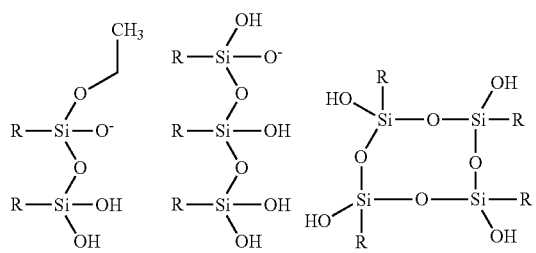

wherein R is any organic residue.

Branching structures can be formed by having more than one reactive position in the monomers (Peleshanko and Tsukruk, Prog. Polym. Sci. 2008, 33)

In some embodiments said polymeric framework comprises branched monomer residues.

In some embodiments said polymeric framework comprises monomer residues that link terminally to more than one other monomer.

In some embodiments said polymeric framework comprises a branched polymer framework selected from the group consisting of polyethyleneimine, modified polyethyleneimine, hyperbranched polyol, and hyperbranched triazine.

A well-known example of a branched random polymer is polyethyleneimine formed by the polymerization of aziridine. Polyethyleneimine contains a mixture of primary, secondary and tertiary amino groups and it has a branching random structure as indicated in the scheme below. The exact structure drawn is only to be construed as typical and in no way limiting to the current invention. The chelating groups such as bisphosphonates, crucial to the current invention, may be attached to the primary and/or secondary amino groups as expanded on below.

In some embodiments of the invention said polymeric framework is polyethyleneimine.

In some embodiments of the invention said polymeric framework is polyethyleneimine with a degree of branching of 40-60%.

Below a typical polyethyleneimine structural fragment is shown, wherein the dashed bonds indicate that the polymeric network continues:

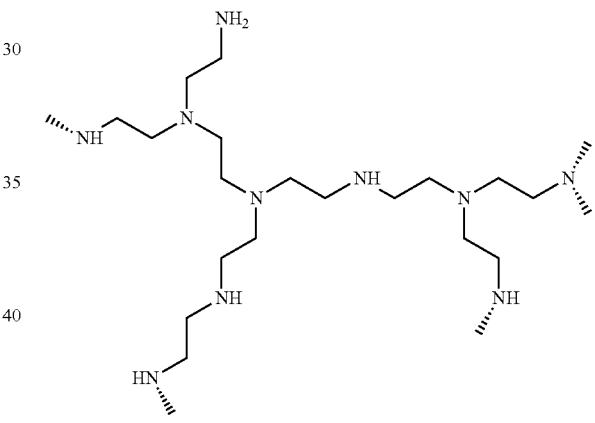

A non-limiting example of a structure that may be advantageous for some embodiments of the present invention is one with said central part comprising a branched polymeric framework based on polyethyleneimine adorned with chelating groups independently selected from the group consisting of —COOR$^1$, —P=O(OR$^1$)(OR$^2$), and —S(=O)$_2$OR$^1$, wherein $R^1$ and $R^2$ are independently selected from the group consisting of a negative charge, H, lower alkyls, and aryl. A useful way of introducing chelating groups in the form of carboxylates is to introduce a DOTA chelator via an amide link as shown below in Scheme 1.

To further optimize the bioinert properties of nanostructures based on polyethyleneimine a number of negatively charged groups such as carboxylates can be introduced to make the whole nanostructure neutral at physiological pH. An established way of doing this is to introduce the carboxylates via treatment with succinic anhydride (Wen et al. J. Appl. Polym. Sci. 2013, 3807).

Said peripheral part, further expanded on below, comprises a multitude of polyethyleneglycol residues covalently attached to the outer parts of said central part. The attachment may take many forms as is well known to one skilled in the art. See e.g. Hermanson, 2nd ed., Bioconjugate Techniques, Greg T. Elsevier 2008, for background on the subject. Some specific ways of binding said polyethyleneglycol residues to said central part are:

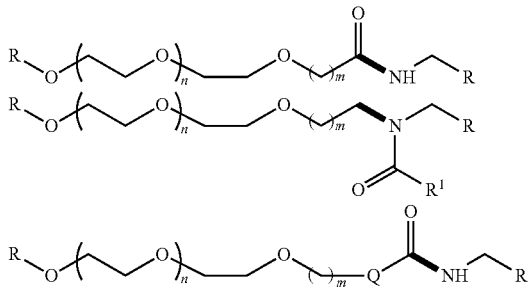

wherein R is said central part with a nitrogen atom suitable for attachment to said peripheral part, n=6-100, m=1-10, Q=O or NH and the covalent bond between said peripheral part and said central part is marked in bold. $R^1$ is H or lower alkyls.

Any mix between branching and crosslinked structure is also useful for the applications considered in the current invention. A non-limiting example is the hyperbranched polyethyleneimine crosslinked by the addition of glutaraldehyde.

Of said chelating groups there are at least four in each nanostructure, arranged in a fashion that allows the chelation of one or more multiply charged cations. The four or more chelating groups may form a pre-organized covalently bound unit already favorable for chelation of a multiply charged cation and attach to the polymeric framework through one or more covalent bonds, optionally with a spacer group in between (see FIG. 4) or; said chelating groups may be randomly distributed through said central part and rely on chance to arrange themselves in a way that allows chelation of said multiply charged cations (see FIG. 3). When relying on chance it is necessary to incorporate a large excess of chelating groups in the central part to get a reasonable probability of forming a cluster of chelating groups with chelating ability.

The inventors have discovered that when chelating groups such as the bisphosphonate structure $R^3R^4C(P=O(OR^1)(OR^2))_2$ wherein $R^1$ and $R^2$ are independently selected from the group consisting of a negative charge, H, lower alkyls, and aryl are incorporated into a polymeric framework, and allowed to bind multiply charged cations they bind said cations strongly.

The phosphonate groups may be completely present in their ester form, completely or partially hydrolyzed to their acid form and subsequently ionized to some extent from partial to complete according to the pH value of the surrounding medium or any mixture thereof. The nanostructures comprising said phosphonate groups bind said multivalent cations best at neutral or basic pH. This indicates that it is, at least in part or sometimes or even completely, the anionic form of the hydrolyzed phosphonate, which plays an important part in the binding of the metal ions. Not only phosphonate esters or acids but also phosphonic amides may be contemplated as part of the material or to be used as starting material.

The number of chelating groups may range from just four to a large number determined by the number of monomer residues in said central part. In Table 1 are shown non-limiting examples of how many monomers and hence how many chelating groups that may realistically be packed into said central part when said central part has various sizes. For simplicity a non-limiting example of typical molecular weight of the monomer fragment was chosen as 200 g/mol and the density of the hypothetical material was set to 1 g/ml.

TABLE 1

| Diameter of central part (nm) | Maximum number of chelating groups |
| --- | --- |
| 6 | 341 |
| 10 | 1580 |
| 15 | 5320 |
| 20 | 12600 |
| 50 | 39400 |
| 70 | 541000 |
| 90 | 1150000 |

Figure 3:
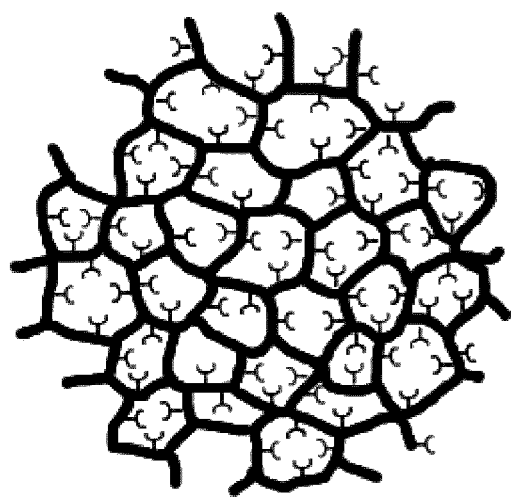
FIG. 3 illustrates how randomly placed chelating groups (semi-circles on a stalk) can be distributed in said central part and by chance form good binding site for multiply charged cations.
Figure 4:
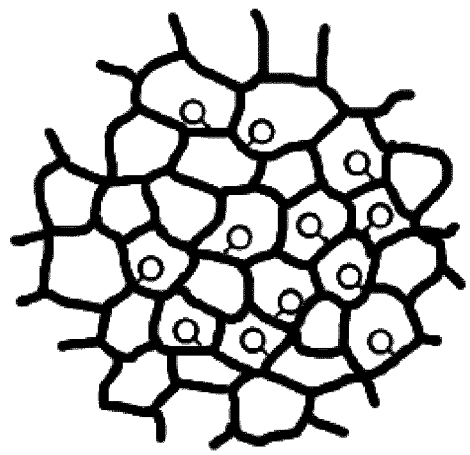
FIG. 4 illustrates how preformed chelators (circles on a stalk) may be incorporated in said central part.

When a pre-organized group is linked to said polymer network it can be chosen from a huge number of known chelating groups, the most well known being EDTA, DTPA and DOTA but in e.g. FIGS. 2 and 3 of Wadas et al., Chem. Rev. 2010, 110 are shown a large number of pre-organized chelators which would be useful for the current invention. Many of them can be covalently linked to said polymeric framework in ways obvious to one skilled in the art. A specific non-limiting example of a covalently bound unit favorable for chelation is the well-known chelator DOTA, which can be covalently bound to the polymer network through an amide bond, as shown below wherein R is said central part:

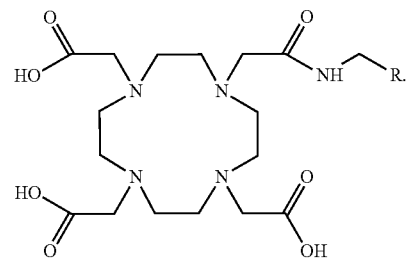

In some embodiments DOTA attached to the polymer network through an amide bond is used as said covalently bound unit favorable for chelation.

When said chelating groups are randomly distributed in the central part acidic groups like carboxylate, phosphate, phosphonate or sulfonate are useful.

In some embodiments said chelating groups are independently selected from the group consisting of —COOR$^1$, —P=O(OR$^1$)(OR$^2$), and —S(=O)2OR$^1$, wherein $R^1$ and $R^2$ are independently selected from the group consisting of a negative charge, H, lower alkyls, and aryl.

In some embodiments said chelating groups comprise geminal bisphosphonate groups wherein said geminal phosphonate groups independently of each other are incorporated as

wherein:

$R^1$ and $R^2$ are independently selected from the group consisting of negative charge, H, lower alkyls, and aryl and >C denotes a carbon atom that is connected to said crosslinked or branched polymeric framework of said central part, or forms a part of said crosslinked, branched or branched polymeric framework of said central part.

When incorporating said chelating groups in a polyacrylate framework it is conceivable to attach said chelating groups to the amide nitrogen through a short linker. A typical but non limiting example of a structural fragment from such a material is the structure below with $R^1$ and $R^2$ as defined earlier in the text, n from 1-5 and the dashed bonds indicating that the fragment belongs to a polymer. It is also conceivable to attach the bisphosphonate directly to the carbon skeleton:

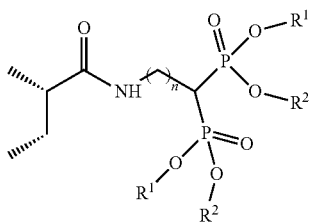

Frameworks based on polyaromatics like polystyrene or polyvinylpyridine can also be envisioned. The chelating groups such as bisphosphonates are then attached to the aromatic system. Polyamides like polyvinylpyrrolidinone are also conceivable.

In some embodiments said chelating groups comprises a multitude of phosphonate groups —P═O(OR$^1$)(OR$^2$) where $R^1$ and $R^2$ are independently selected from a negative charge, H, alkyl or aryl. When at least one of $R^1$ or $R^2$ is H the resulting phosphonic acid is ionized to a pH dependent extent.

In some embodiments of the invention $R^1$ and $R^2$ are independently a negative charge, H or methyl.

In some embodiments said phophonate groups are incorporated pairwise as geminal bisphosphonates, also called 1,1-bisphosphonates.

To the carbon atom separating the bisphosphonate groups, i.e. the intervening carbon atom, one or more bonds to the polymeric framework are present. Of particular interest are the structures of the type $(R^{20}R^{21}C(P═O(OR^1)(OR^2))_2$ where $R^1$ and $R^2$ are independently selected from H or alkyl or aryl and at least one of $R^{20}$ and $R^{21}$ is a group capable of being connected to the polymeric framework of the material. In the case where only one of $R^{20}$ and $R^{21}$ is such a group, the remaining group is selected from H, OH, OR$^{22}$, (with $R^{22}$ being lower alkyls) or lower alkyls.

In some embodiments of the present invention $R^{20}$ is —(CH$_2$)$_n$CO— (with the carbonyl group forming the bond to the polymeric framework) and $R^{21}$ is H or OH and n=1-5. In some of these embodiments n=1.

In some embodiments of the present invention $R^{20}$ and $R^{21}$ are independently —(CH$_2$)$_n$—SiO$_3$, where n=1-5 and the silane is part of the polymeric framework by the formation of Si—O—Si bonds as expanded upon later in the text.

In some embodiments of the present invention $R^{20}$ and $R^{21}$ are both —(CH$_2$)$_n$—SiO$_3$, wherein n=3 and the silane is part of said polymeric framework in the above manner.

It is also conceivable to use phosphonic amides, chlorides or fluorides instead of phosphonic esters or acids as components or starting materials of the compounds described here. The phosphonates may be present in their free form or as esters or as amides or any mixture thereof.

In some embodiments of the invention the phosphonates are a mixture of free phosphonates and the methyl esters of said phosphonate.

When incorporating said chelating groups in a polyethylene framework it is conceivable to attach said chelating groups either directly to the hydrocarbon network or via the primary introduction of a heteroatom such as a primary or secondary amine nitrogen through a short linker. A typical but non limiting example of a structural fragment from such a material when the chelating group is a geminal bisphosphonate, is the structure below with $R^1$ and $R^2$ as defined earlier in the text, n from 1-5, and R is the polymeric framework of said polyethyleneimine:

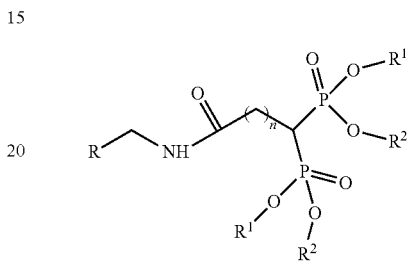

The purpose of the peripheral part is to impart the whole nanostructure with the property of being bioinert, i.e. not interacting with an organism such as a mammal e.g. a human. It is desirable that the nanostructures are not degraded to any substantial degree when introduced in said organism to avoid loss of parts of the material.

Figure 5:
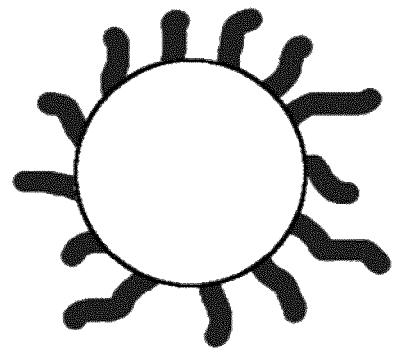
FIG. 5 illustrates a nanostructure with central part marked in white and the covalently linked linear polymer chains of the peripheral part marked in black.
Figure 6:
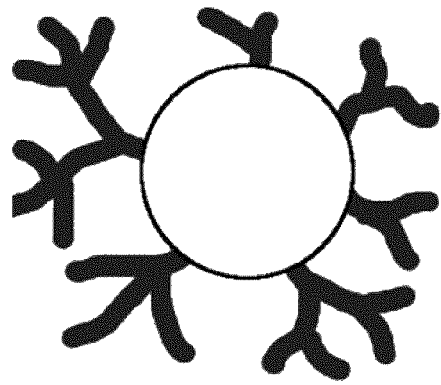
FIG. 6 illustrates a nanostructure with central part marked in white and the covalently linked branched polymer chains of the peripheral part marked in black.
Figure 7:
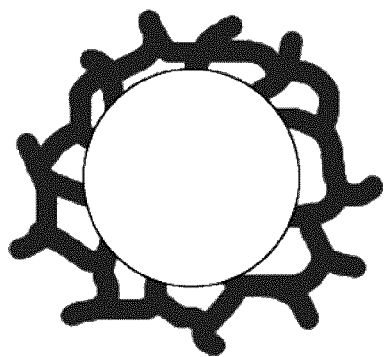
FIG. 7 illustrates a nanostructure with central part marked in white and the covalently linked crosslinked polymer chains of the peripheral part marked in black.

Said peripheral part of said nanostructure comprises a polymeric material selected from the group consisting of synthetic polymeric materials and carbohydrate materials, wherein said polymeric material is hydrophilic and bioinert, and where said polymeric material further is electrically neutral or zwitterionic and wherein said polymeric material is covalently linked to said central part. Said peripheral part may comprise linear, branched or crosslinked polymers, see FIG. 5-7.

In some embodiments said peripheral part comprises polymeric materials independently selected from the group consisting of A-(O—CH$_2$CH$_2$)$_n$OR$^9$, wherein n=2-100, and $R^9$ is a H or lower alkyls and A is a group that is linked to or incorporated into said polymeric framework and said group is selected from the group consisting of:

—OSi(R$^{10}$)$_2$(CH$_2$)$_m$—, wherein $R^{10}$ is selected from the group consisting of H or C$_1$-C$_8$ hydrocarbons and m=2-5;

—OSi(OR$^{11}$)$_2$(CH$_2$)$_m$—, wherein $R^{11}$ is independently selected from the group consisting of a covalent bond to the polymeric framework, H and C$_1$-C$_8$ hydrocarbons, and m=2-5;

—NR$^{11}$—C═O—(CH$_2$)$_m$—, wherein $R^{11}$ is as above and m=2-5

—O—C═O—(CH$_2$)$_m$—, wherein m=2-5;

—NR$^{11}$—(CH$_2$)$_m$—, wherein $R^{11}$ is as above and m=2-5;

—(CH$_2$)$_m$, wherein m=2-5;

—O—(CH$_2$)$_m$—, wherein m=2-5; and

—SX$_2$—(CH$_2$)$_m$—, wherein X is independently nothing or O and m=2-5.

In some embodiments the peripheral part comprises a covalently attached linear, neutral, synthetic, bioinert, hydrophilic polymer.

In some embodiments the peripheral part comprises a covalently attached derivative of polyethyleneglycol.

In some embodiments the peripheral part comprises a covalently attached derivative of methyl terminated polyethyleneglycol.

In some embodiments the peripheral part comprises a covalently attached branched derivative of polyethyleneglycol.

In some embodiments the peripheral part comprises a covalently attached branched derivative of polyethyleneglycol such as:

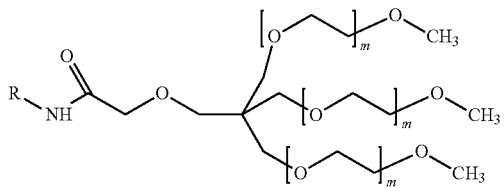

where R is said central part and m is independently 3-100.

In some embodiments said peripheral part is zwitterionic, i.e. contains a multitude of positive and negative charges, in a 1:1 ratio, rendering the total electrically neutral.

In some embodiments said peripheral part comprises crosslinked polyacrylamide.

In some embodiments said peripheral part comprises dextran.

Figure 8:
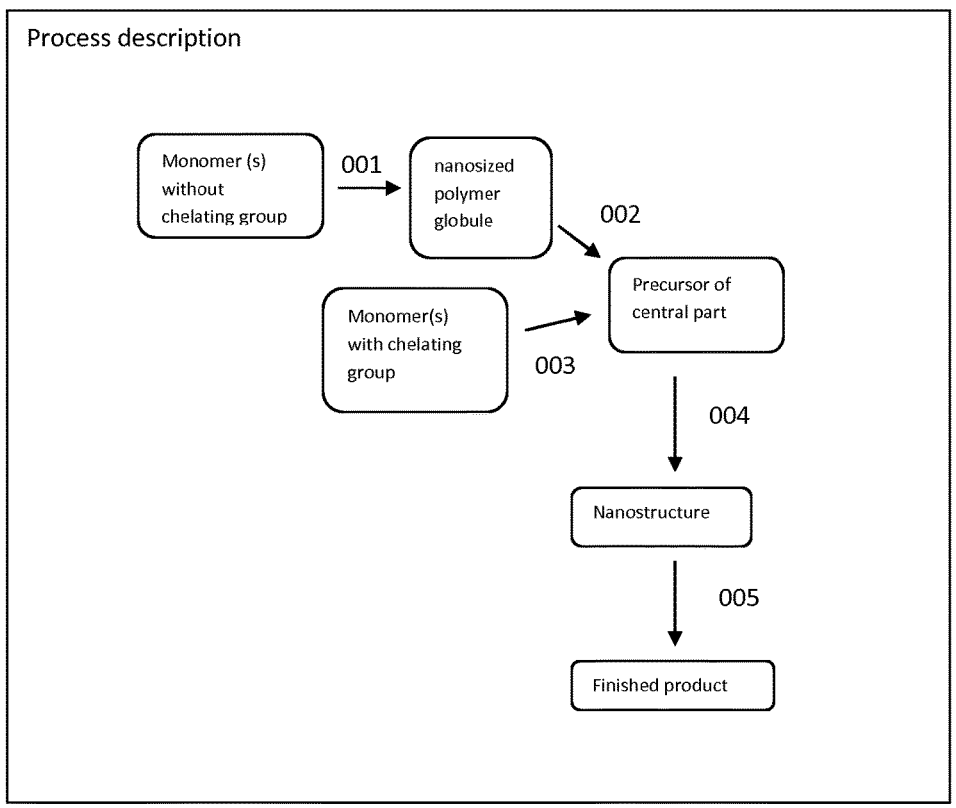
FIG. 8 is a schematic illustration of a process that may be used for producing the nanostructures.

The second major aspect of the current invention is a process to produce said nanostructures. A schematic illustration of such a process is shown in FIG. 8. In its broadest sense it first involves the formation or acquisition of globular, nanosized polymer entities (001 in FIG. 8), later ending up comprising said central part of said nanostructures, and in no particular order followed by a step (002 in FIG. 8), which may sometimes be included in the first step (003 in FIG. 8) when said monomers already carry chelating groups or precursors of said chelating groups, introducing a multitude of chelating groups, and in no particular order, followed by a step (004 in FIG. 8) where the product of the first step(s) is contacted precursors to said peripheral apart. Optionally, the three steps, although chemically distinct, may be carried out simultaneously in the same reaction vessel. At one or more instances of the process a size selection or purification step (005 in FIG. 8) by ultrafiltration or some other method of size selection, is incorporated. Step (004 in FIG. 8) may sometimes be performed before step (002 in FIG. 8). It is usually beneficial to exclude air from the reaction vessels used in the process to obtain a product of good quality. Filling the process equipment with nitrogen gas is a useful way of excluding air.

A nanosized polymer globule comprising a multitude of chelating groups such as bisphosphonates is obtained either via grafting (002 in FIG. 8) to an existing polymer globule (obtained by a polymerization step 001 in FIG. 8) or by polymerization of a monomer mixture comprising chelating groups such as bisphosphonates (003 in FIG. 8). Depending on which polymeric framework is desired, many different polymerization initiators can be contemplated. For unsaturated monomers like styrenes and acrylates various radical initiators, such as benzoylperoxide or azobisisobutyronitrile, or their water soluble analogs are preferred. For the trialkoxy silane based monomers of one of the preferred embodiments of the current invention, it is possible to use spontaneous hydrolysis and condensation to effect the polymerization or to use acid or base catalysis.

Often a solvent is desirable for step 003 and although many different ones can be envisioned by one skilled in the art, it is desirable to avoid toxic solvents so water and lower alcohols such as propanol, butanol, ethylene glycol, or 1,3-propanediol are preferred. It is often desirable to optimize the yield and quality of the product by using mixtures of solvents.

In some embodiments of the process a mixture of 5-25% of water in a lower alcohol is used in step 003.

In some embodiments of the process a mixture of 5-25% of water in ethanol, 1- or 2-propanol or 1,2- or 1,3-propanediol or ethyleneglycol is used in step 003.

In some embodiments of the present invention, it has been found to be advantageous to use temperatures higher than room temperature for step 003 such as temperatures between 40 and 130° C. or between 80 and 120° C. or between 100 and 120° C. When lower alcohols are used it is necessary to work with closed pressure resistant vessels to achieve the desired reaction temperature.

The duration of step 003 depends on the polymeric framework and mode of initiation and may range from seconds to days. For the trialkoxy silanes in one of the preferred embodiments of the current invention, it has proven advantageous to use times from 6 hours to 48 hours or from 12 to 36 hours or times around 24 hours in step 003.

In some embodiments of the invention the conditions of step 003 are a temperature of 105-115° C. and a duration from 20 to 30 hours.

In some embodiments of the invention the conditions of step 003 are a temperature of 105-115° C. and a duration from 30 to 60 hours.

In some embodiments of the invention the conditions of step 003 are a temperature of first 90-100° C. for 40-50 hours and then 105-115° C. for another 20 to 30 hours.

The concentration of monomers in step 003 depends on which polymeric framework is desired and can range from a molar concentration to solvent free conditions. However, for the trialkoxy silanes in one of the preferred embodiments of the current invention, it has proven advantageous to work from 10 mM to 500 mM or 20-100 mM and in particular from 40-80 mM monomer concentration.

In some embodiments of the invention the conditions of step 003 are first a temperature of 90-100° C. for 20 to 50 hours followed by 105-125° C. for to 30 hours and a monomer concentration of 40-60 mM.

In step 002 which involves the grafting of a bisphosphonate reagent to a polymeric framework the conditions are somewhat different. Especially the demands on temperature and concentration are more lenient. The inventors have found that starting with a solution of polyethyleneimine in water optionally with the admixture of a cosolvent, at a temperature compatible with liquid water, such as room temperature and contacting it with a bisphosphonate capable of reacting with said polyethyleneimine, such as 3,3-bis (dimethoxyphosphoryl)propanoic acid, in the presence of a compound capable of forming a reactive ester intermediate, such as N-hydroxysulfosuccinimide sodium salt in the presence of a coupling agent, such as N-(dimethylaminopropyl)-N"-ethyl carbodiimide at a temperature, such as room temperature for a time period of 1-48 hours, such as 20-24 hours, produce a material with bisphosphonates grafted to the polymeric framework.

A size selection step (005) is performed on the solution of nanostructures to remove undesirably large or small entities. Starting materials and solvent residues from the reaction mixture are also removed at this stage. Ultrafiltration is a preferred method of purification, especially when used in the form which is usually labeled tangential flow filtration or diafiltration. It is preferred to remove undesirably large nanostructures and/or aggregates by passing the solution through a filter with rather large pores, step 005a. Preferred nominal cut-off values for such filters are 0.2 um, 1000 kDa, or 300 kDa. In a step 005b the desired material is collected on a filter with smaller pore size. Preferred pore sizes for step 005b have nominal cut-off values at 300 kDa, 100 kDa, 50 kDa, 30 kDa, or 10 kDa, with the proviso that when a 300 kDa filter is used in step 005b, the filter used in step 005a must have larger pores.

The size selection step (004) may not be required if the starting material has a narrow size distribution.

In some embodiments of the invention a solution obtained from process step 002 or 003 is passed, first through a 500 kDa filter (step 004a) and, subsequently, collected on a 100 kDa filter (step 004b).

In some embodiments of the invention a solution obtained from process step 002 or 003 is passed first through a 300 kDa filter (step 004a) and subsequently collected on a 100 kDa filter (step 004b).

It is advantageous to wash the material with several portions of water after step 004b to further remove unreacted monomers or solvent residues from step 001, 002 or 003.

Other ultrafiltration methods such as spin filters or dialysis can also be used although they are less scalable.

Particles of the desired size range may also be selected by size exclusion chromatography (also called gel filtration).

Optionally, said nanostructures may be purified in a step 007. Step 007 may have several substeps 007a, 007b etc of, for a substep in no particular order, 007x.

One preferred method of a purification step 007x is treatment with a small amount of silica to remove unreacted precursor of said peripheral part.

In some embodiments of the invention step 007x involves yet another diafiltration collecting the material on a filter.

Subsequent purification steps 007x to remove lipophilic impurities such as traces of endotoxins (residues of dead bacteria) may also be added.

In some embodiments of the process the product of step 006 is treated with activated charcoal.

In some embodiments the process the product of step 006 is passed through a polyethylene, or polypropylene, or PVDF filter.

In some embodiments of the process the product of step 006 is treated with immobilized polymyxin B.

In some embodiments, the globular nanostructure may be produced by a process comprising the steps of:

1) forming a central part by a hydrolytic polymerization of a disilane of the structure

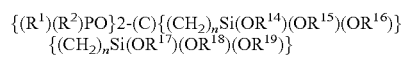

wherein $R^1$ and $R^2$ are independently selected from the group consisting of negative charge, H, lower alkyls, and aryl and $R^{14}$, $R^{15}$, $R^{16}$, $R^{17}$, $R^{18}$, and $R^{19}$ are independently selected from the group consisting of lower alkyls and aryl; and n=1-5; and 2) contacting said central part with a precursor of the peripheral part under conditions conducive to said part covalently linking to said central part.

In the third major aspect of the invention, said nanostructure chelates a radionuclide.

In some embodiments the hydrodynamic diameter of said nanostructure, which is that of the first aspect of the invention, is between 8 and 100 nm and said nanostructure chelates a radionuclide for imaging and/or radiotherapy.

In some embodiments the hydrodynamic diameter of said nanostructure of is between 8 and 100 nm and said nanostructure chelates a radionuclide for imaging.

In some embodiments the hydrodynamic diameter of said nanostructure is between 8 and 100 nm and said nanostructure chelates a radionuclide for radiotherapy.

In some embodiments the hydrodynamic diameter of said nanostructure is between 8 and 50 nm and said nanostructure chelates a radionuclide for imaging and/or radiotherapy.

In some embodiments the hydrodynamic diameter of said nanostructure of is between 8 and 50 nm and said nanostructure chelates a radionuclide for imaging.

In some embodiments the hydrodynamic diameter of said nanostructure is between 8 and 50 nm and said nanostructure chelates a radionuclide for radiotherapy.

In some embodiments the hydrodynamic diameter of said nanostructure is between 8 and 20 nm and said nanostructure chelates a radionuclide for PET imaging.

In some embodiments the hydrodynamic diameter of said nanostructure is between 8 and 20 nm and said nanostructure chelates a radionuclide for PET imaging such as gallium-68 ($^{68}$Ga).

In some embodiments the hydrodynamic diameter of said nanostructure is between 8 and 20 nm and said nanostructure chelates a radionuclide for SPECT imaging.

In some embodiments the hydrodynamic diameter of said nanostructure is between 8 and 20 nm and said nanostructure chelates a radionuclide for SPECT imaging such as technetium-99m in its tri-cationic form ($^{99m}Tc^{3+}$).

In some embodiments the hydrodynamic diameter of said nanostructure is between 8 and 20 nm and said nanostructure chelates a radionuclide for radiotherapy.

In some embodiments the hydrodynamic diameter of said nanostructure is between 8 and 20 nm and said nanostructure chelates yttrium-90 ($^{90}Y$).

In some embodiments the hydrodynamic diameter of said nanostructure is between 8 and 20 nm and said nanostructure chelates a radionuclide for PET imaging such as gallium-68 ($^{68}$Ga) and a radionuclide for radiotherapy such as yttrium-90 ($^{90}Y$).

In some embodiments the hydrodynamic diameter of said nanostructure is between 8 and 20 nm and said nanostructure chelates a radionuclide for SPECT imaging such technetium-99m ($^{99m}Tc^{3+}$) and a radionuclide for radiotherapy such as yttrium-90 ($^{90}Y$).

In some embodiments the hydrodynamic diameter of said nanostructure is between 8 and 20 nm and said nanostructure chelates a radionuclide for imaging and/or radiotherapy such as lutetium-177 ($^{177}Lu$).

In some embodiments the central part of said nanostructure of the first aspect of the invention comprises a polymeric framework where said polymeric framework is derived from polyalkenes, polyacrylates, polymethacrylates, polyamides, polystyrene, polydimethylsiloxanes (silicones), polyorganosilanes, polyamines such as polyethyleneimine, or carbohydrates, chelating radionuclides for imaging and/or radiotherapy.

In some embodiments the central part of said nanostructure comprises a polymeric framework where said polymeric framework is derived from polyalkenes, polyacrylates, polymethacrylates, polyamides, polystyrene, polydimethylsiloxanes (silicones), polyorganosilanes, polyamines such as polyethyleneimine, or carbohydrates, chelating radionuclides for imaging.

In some embodiments said central part of said nanostructure comprises a polymeric framework where said polymeric framework is derived from polyalkenes, polyacrylates, polymethacrylates, polyamides, polystyrene, polydimethylsiloxanes (silicones), polyorganosilanes, polyamines such as polyethyleneimine, or carbohydrates, chelating radionuclides for radiotherapy.

In some embodiments said central part of said nanostructure comprises a polymeric framework where said polymeric framework is a polyorganosilane and said nanostructure chelates a radionuclide for PET imaging such as gallium-68 ($^{68}$Ga).

In some embodiments said central part of said nanostructure comprises a polymeric framework where said polymeric framework is a polyorganosilane and said nanostructure chelates a radionuclide for SPECT imaging such as technetium-99m ($^{99m}$Tc$^{3+}$).

In some embodiments said central part of said nanostructure comprises a polymeric framework where said polymeric framework is a polyorganosilane and said nanostructure chelates a radionuclide for radiotherapy such as yttrium-90 ($^{90}$Y).

In some embodiments said central part of said nanostructure comprises a polymeric framework where said polymeric framework is a polyorganosilane chelating a radionuclide for PET imaging such as gallium-68 ($^{68}$Ga) and a radionuclide for radiotherapy such as yttrium-90 ($^{90}$Y).

In some embodiments said central part of said nanostructure comprises a polymeric framework where said polymeric framework is a polyorganosilane chelating a radionuclide for SPECT imaging such as technetium-99m ($^{99m}$Tc$^{3+}$) and a radionuclide for radiotherapy such as yttrium-90 ($^{90}$Y).

In some embodiments said central part of said nanostructure comprises a polymeric framework where said polymeric framework is a polyorganosilane chelating radionuclides for imaging and/or radiotherapy such as lutetium-177 ($^{177}$Lu).

In some embodiments said central part of said nanostructure comprises a branched polymer framework chelating a radionuclide for imaging and/or radiotherapy.

In some embodiments said central part of said nanostructure comprises a branched polymer framework chelating a radionuclide for imaging.

In some embodiments said central part of said nanostructure comprises a branched polymer chelating a radionuclide for radiotherapy.

In some embodiments said central part of said nanostructure comprises a branched polymer framework comprising polyethyleneimine comprising a chelated radionuclide for PET imaging such as gallium-68 ($^{68}$Ga).

In some embodiments said central part of said nanostructure comprises a branched polymer framework comprising polyethyleneimine comprising a chelated radionuclide for SPECT imaging such as technetium-99m ($^{99m}$Tc$^{3+}$).

In some embodiments said central part of said nanostructure comprises a branched polymer framework comprising polyethyleneimine comprising a chelated radionuclide for radiotherapy such as yttrium-90 ($^{90}$Y).

In some embodiments said central part of said nanostructure comprises a branched polymer framework comprising polyethyleneimine comprising a chelated a radionuclide for PET imaging such as gallium-68 ($^{68}$Ga) and a chelated radionuclide for radiotherapy such as yttrium-90 ($^{90}$Y).

In some embodiments said central part of said nanostructure comprises a branched polymer framework comprising polyethyleneimine comprising a chelated radionuclide for SPECT imaging such as technetium-99m ($^{99m}$Tc$^{3+}$) and a radionuclides for radiotherapy such as yttrium-90 ($^{90}$Y).

In some embodiments said central part of said nanostructure comprises a branched polymer framework comprising polyethyleneimine comprising a chelated a radionuclide for imaging and/or radiotherapy such as lutetium-177 ($^{177}$Lu).

In some embodiments said central part chelates a radionuclide for imaging and/or radiotherapy where said peripheral part comprises polymeric materials independently selected from the group consisting of A-(O—CH$_2$CH$_2$)$_m$OR$^9$, wherein m=2-100, and R$^9$ is a H or lower alkyls and A is a group linked to or incorporated into said polymeric framework and said group is selected from the group consisting of:

—OSi(R$^{10}$)$_2$(CH$_2$)$_o$—, wherein R$^{10}$ is selected from the group consisting of H or C1-C8 hydrocarbons and o=2-5;

—OSi(OR$^{11}$)$_2$(CH$_2$)$_o$—, wherein R$^{11}$ is independently selected from the group consisting of a covalent bond to the polymeric framework, H and C1-C8 hydrocarbons, and o=2-5;

—NR$^{10}$—C=O—(CH$_2$)$_m$—, wherein R$^{10}$ is as above and m=2-5

—O—C=O—(CH$_2$)$_m$—, wherein m=2-5;

—NR$^{10}$—(CH$_2$)$_m$—, wherein R$^{10}$ is as above and m=2-5;

—(CH$_2$)$_m$—, wherein m=2-5;

—O—(CH$_2$)$_m$—, wherein m=2-5; and

—SX$_2$—(CH$_2$)$_m$—, wherein X is independently nothing or O and m=2-5.

In some embodiments comprising a plurality of said nanostructures, the average number of radionuclides chelated to each of said nanostructures is between 0.1-20 000/nanostructure where said radionuclide is a radionuclide for imaging and/or radiotherapy.

In some embodiments comprising a plurality of said nanostructures the average molecular weight of said nanostructures is between 50 000 and 300 000 000 Da where said nanostructures chelate radionuclides for imaging and/or radiotherapy with the proviso that the average hydrodynamic diameter of said nanostructures is 8-100 nm.

In the Fourth Aspect of the invention, a method of obtaining a composition comprising nanostructures comprising radionuclides, wherein a plurality of nanostructures according to the first aspect of the invention is contacted with at least one radionuclide, is provided.

In the Fifth major aspect of the invention, a composition comprising a plurality of said nanostructures comprising a radionuclide for imaging and/or radiotherapy is used as an imaging and/or radiotherapeutic agent for diagnostic and/or radiotherapeutic procedures. The composition comprising a plurality of said nanostructures comprising a radionuclide for imaging and/or therapy can be used to diagnose, deliver radiotherapy as well as monitor the response to radiotherapy.

Said compositions comprising a radionuclide for imaging and/or radiotherapy described herein can be contemplated for the treatment and/or diagnosis of any disease, disorder and/or condition featuring leaky microvasculature, such as cancer and inflammatory conditions.

The compositions of nanostructures comprising a radionuclide for imaging and/or radiotherapy in accordance with the present invention may be used to treat, alleviate, ameliorate, relieve, delay onset of, inhibit progression of, reduce severity of, reduce adverse effects of a combination therapy, and/or reduce incidence of one or more symptoms or features of that disease, disorder, and/or condition in species that include, but are not limited to, humans and/or other primates; mammals, including commercially relevant mammals such as cattle, pigs, horses, sheep, cats, and/or dogs; and/or birds.

This aspect of the invention also relates to a method for administering compositions comprising a radionuclide for imaging and/or radiotherapy according to the current invention to a subject suffering from cancer. Such methods comprise administering a therapeutically effective amount of inventive nanostructures comprising a radionuclide for imaging and/or radiotherapy to a subject in such amounts and for such time as is necessary to achieve the desired result (i.e. treat, alleviate, ameliorate, relieve, delay onset of, inhibit progression of, reduce severity of, reduce adverse effects of a combination therapy, and/or reduce incidence of one or more symptoms or features of cancer).

In some embodiments, said composition of said nanostructures comprising a radionuclide for imaging and/or radiotherapy may be used to diagnose and/or treat soft tissue tumors.

In some embodiments, said composition of said nanostructures comprising a radionuclide for imaging and/or radiotherapy may be used to diagnose and/or treat metastatic disease.

In some embodiments, administration of a composition of said nanostructures comprising a radionuclide for imaging is used to diagnose disease and thereafter, administration of said composition of said nanostructures comprising a radionuclide for radiotherapy, is used to treat soft tissue tumors.

The in-vivo use of the nanostructures of this invention requires them to be formulated in a composition in a pharmacologically acceptable way according to best practice well known to those skilled in the art. According to the present invention, a composition comprising the nanostructures may be administered to a subject in need in a manner which ensures the delivery of the nanostructures to tissues comprising leaky microvasculature. Such administration may ensure that the nanostructures are brought into circulation in the blood or the lymph. The preferred mode of administration is thus parenteral, and specifically intravenous injection, however, other routes of administration such as oral, transdermal, transmucosal, intraperitoneal, intracranial, intraocular, epidural, intrathecal, intranasal, topical, rectal, vaginal, pulmonary route are contemplated.

Parenteral administration often requires a liquid formulation. Water is a preferred solvent to bring the nanostructures of the current invention into solution but one or more co-solvents or additives may be added in 0.1-10% to improve stability in solution. Acceptable co solvents are alcohols like ethanol or glycerol, biocompatible polymers like polyethyleneglycol or polyvinyl alcohol, dimethyl sulfoxide, or N-methyl pyrrolidinone. It can also be advantageous to add one or more osmoregulators like mannitol, sorbitol, lactose, glucose or other sugars or sugar alcohols. It is desirable that the formulation is isoosmotic with the body fluids. Preferably, the solution for intravenous use has an osmolality from 270-2000 mOsm or 280-1000 mOsm or 280-500 mOsm or in particular from 280-300 mOsm. Many of said additives may also fulfill the function of cryoprotectants, enhancing the efficiency of reconstitution after freeze drying. It may also be advantageous to add electrolytes to lower the physiological effects of the injected solution. Preferred electrolytes would be a combination of non toxic salts of sodium, calcium or and/or magnesium. Regulation of the pH of the injectable solution is preferable and any buffer suitable for injection can be contemplated but preferred is Tris-HCl.

A rectally administrable formulation or a formulation that is rectally administered may be essentially isoosmotic with biological fluids, typically 290 mOsm. The osmotic potential is regulated by adding small molecule osmoregulators, such as sodium chloride or mannitol. The formulation is of a volume sufficient to fill the part of colon of interest and may be a free flowing liquid or it may have viscosity modifying additives like high molecular weight polyethylene glycol (PEG) for improved handling. It may be formulated as a foam or foamable preparation to achieve a large volume without requiring a large volume of liquid.

In some embodiments the composition is formulated for parenteral injection.

In some embodiments the composition is formulated for intravenous injection.

In some embodiments the composition is formulated for rectal administration in the form of a liquid such as a retention enema.

It will be appreciated that the exact dosage of the nanostructure or components thereof, such as a radionuclide, may be determined by a physician in view of the patient to be treated. In general, dosage and administration are adjusted to provide an effective amount of the inventive conjugate to the patient being treated. As used herein, the "effective amount" refers to the amount necessary to elicit the desired biological response. As will be appreciated by those of ordinary skill in this art, the effective amount may vary depending on such factors as the desired biological endpoint, the radionuclide to be delivered, the target tissue, the route of administration, etc. Additional factors which may be taken into account include the severity of the disease state; age, weight and gender of the patient being treated; diet, time and frequency of administration; radionuclide combinations; and tolerance/response to radiotherapy.

For any composition, the therapeutically effective dose can be estimated initially by calculation, in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of compositions can be determined by standard pharmaceutical procedures in cell cultures or experimental animals, e.g., ED50 and LD50. The dose ratio of toxic to therapeutic effects is the therapeutic index, and it can be expressed as the ratio, LD50/ED50.

Any radionuclide could be contemplated for any imaging purposes; however, radionuclides meeting the criteria of emitting a suitable type of radiation with suitable half-lives especially suited for diagnostic imaging applications are preferred in the current invention. Ideal radioisotopes for diagnostic applications are those with relatively short half-life, and those with high penetrating radiation to be detected by imaging techniques such as PET and/or SPECT. The half-life of the radionuclide must allow accumulation in the target tissue in the patient while allowing clearance through the non-target organs. Imaging includes imaging for diagnosis, monitoring the effects of treatment, or monitoring the location and dose of nanostructures used for radiotherapy. The incorporation of a radioisotope for imaging in a nanostructure has the advantage of allowing in vivo tracking of the nanostructures and dosimetry in a subject. For example, the biodistribution and/or elimination of the nanostructures may be studied. A better understanding of the biodistribution or elimination of the nanostructures may be used to alter the treatment of patient. For example, more or less nanostructures may need to be used in the treatment of the subject. If the accumulation of nanostructures in the tumor(s) is very good, less of said nanostructures comprising said radionuclides may be needed. If the accumulation in a particular patient is poor, more nanostructures may be needed or the attending physician may resort to a different treatment altogether.

In some embodiments, a composition of nanostructures comprising radionuclides for imaging is used for imaging of a subject.

In some embodiments of the invention, the radionuclide for imaging in the composition of said nanostructures comprises technetium-99m in a trivalent cationic form ($^{99m}Tc^{3+}$) and is used for imaging of a subject.

In some embodiments of the invention, the radionuclide for imaging in the composition of said nanostructures comprises radionuclides for PET imaging and is used for imaging of a subject.

In some embodiments of the invention, the radionuclide for imaging in the composition of said nanostructures comprises gallium-68 (68Ga) and is used for imaging of a subject.

In some embodiments of the invention, the radionuclide for imaging in the composition of said nanostructures comprises radionuclides for SPECT imaging and is used for imaging of a subject.

In some embodiments, the imaging technique used is positron emission tomography (PET).

In some embodiments, the imaging technique used is single photon emission computed tomography (SPECT).

Any radionuclide could be used for radiotherapy; however, radionuclides meeting the criteria of emitting a suitable type of radiation with suitable half-lives are especially suited for radiotherapeutic applications are preferred in the current invention. Ideal radionuclides for therapeutic applications are those with low penetrating radiation, such as β and α-emitters. When the emitting radioisotope in the form of a radiopharmaceutical reaches the target site, the energy emitted is only deposited at the target site and nearby normal tissues are minimally irradiated. The energy of the emitted particles from the different radioisotopes and their ranges in tissues will vary, as well as their half-life, and the most appropriate radioisotope will be different depending on the application, the disease and the accessibility of the disease tissue.

In some embodiments of the invention, the radionuclide for radiotherapy in the composition of said nanostructures comprises radionuclides for radiotherapy and is used for treating a subject.

In some embodiments of the invention, the radionuclide for radiotherapy in the composition of said nanostructures comprises yttrium-90 ($^{90}Y$) and is used for treating a subject.

Many radionuclides can be envisaged for combined diagnostic imaging and therapeutic purposes; however, radionuclides meeting the criteria of emitting a suitable type of radiation with suitable half-lives are especially suited for combined diagnostic imaging and therapeutic applications of the current invention. Ideal radionuclides for diagnostic imaging and therapeutic applications are those with low penetrating radiation, such as β and α-emitters in combination with radionuclide with high penetrating radiation to be detected by imaging techniques such as PET and/or SPECT. Radionuclides emitting both high and low-penetrating radiation can are also contemplated. The half-life of the radionuclide/radionuclides must allow accumulation in the target tissue in the patient while allowing clearance through the non-target organs.

In some embodiments, a composition of nanostructures comprising radionuclides for imaging and/or therapy is used for imaging and/or therapy of a subject.

In some embodiments, a composition of nanostructures comprising non-radioactive isotopes of said radionuclides as well as radionuclides for imaging and/or therapy is used for imaging and/or therapy of a subject.

In some embodiments, radionuclides for imaging and/or radiotherapy in the composition of said nanostructure comprises radionuclides for PET imaging and radiotherapy and are used for imaging and/or radiotherapy.

In some embodiments, radionuclides for PET imaging and radiotherapy in the composition of said nanostructures comprises gallium-68 ($^{68}Ga$) and yttrium-90 ($^{90}Y$) and are used for imaging and/or radiotherapy.

In some embodiments, radionuclides for imaging and/or radiotherapy in the composition of said nanostructure comprises radionuclides for SPECT imaging and radiotherapy and are used for imaging and/or radiotherapy.

In some embodiments, radionuclides for imaging and/or radiotherapy in the composition of said nanostructure comprises technetium-99m ($^{99m}Tc^{3+}$) and yttrium-90 ($^{90}Y$) and are used for imaging and/or radiotherapy.

In some embodiments, the radionuclide for imaging and/or radiotherapy in the composition of said nanostructure comprises lutetium-177 ($^{177}Lu$) and is used for imaging and/or radiotherapy.

In accordance with the Sixth Aspect of the invention a plurality of said nanostructures are provided in a kit. Kits typically include instructions for use of the inventive particles. Instructions may, for example, comprise protocols and/or describe conditions for production of the inventive nanostructures, and administration of the inventive structures to a subject in need thereof, etc. Kits will generally include one or more vessels or containers so that some or all of the individual components and reagents may be separately contained. Kits may also include a means for enclosing individual containers in relatively close confinement for commercial sale, e.g., a plastic box. An identifier, such as a bar code, may be present in or on the kit or in one or more of the vessels or containers included in the kit. An identifier can be used to uniquely identify the kit for purposes of quality control or inventory control.

In some embodiments of the sixth major aspect of the invention, the present invention relates to a kit comprising:
  a. a plurality of nanostructures; and
  b. an aqueous buffer with a pH of 6-7.5 and an osmolality of 500-2000 mOsm/kg, comprising one or more pH regulators and
  c. a composition containing a radionuclide in cationic form.

In some embodiments of said kit, said kit is for preparation of nanostructures comprising radionuclides, and said radionuclides are provided separately from the kit. Therefore said kit comprises:
  a. a plurality of nanostructures, and
  b. an aqueous buffer with a pH of 6-7.5 and an osmolality of 500-2000 mOsm/kg, comprising one or more pH regulators.

In some embodiments, the composition containing the radionuclide is either in storage or delivered from the manufacturer depending on the characteristics of the particular radionuclide.

If the radionuclide is e.g. the positron emitter $^{64}Cu$, said radionuclide is delivered directly from a cyclotron facility to the venue of treatment or diagnosis immediately prior to use, in the form of a (lyophilized) salt or an aqueous solution. Before administration of the radionuclide-containing nanostructures, parts a, b, and c of the kit are mixed and the efficiency of binding is tested, preferably using the simple test procedure supplied with the kit. Following administration the patient may receive a PET- or a SPECT scan. Optimal visualization may be achieved 1-24 hours after administration.

In some embodiments of the disclosed kit described herein the kit comprises a radionuclide for radiotherapy.

In some embodiments of the disclosed kit, the kit of parts comprises a radionuclide for radiotherapy such as yttrium-90 ($^{90}Y$).

In some embodiments of the invention, the kit comprises a radionuclide for imaging.

In some embodiments of the disclosed kit, the kit comprises a radionuclide for imaging such as technetium-99m ($^{99m}Tc^{3+}$).

In some embodiments of the disclosed kit, the kit comprises a radionuclide for PET imaging.

In some embodiments of the disclosed kit, the kit comprises a radionuclide for PET imaging such as gallium-68 ($^{68}Ga$).

In some embodiments of the disclosed kit, the kit comprises a radionuclide for SPECT imaging.

In some embodiments of the disclosed kit, the kit comprises a radionuclide for SPECT imaging such as technetium-99m ($^{99m}Tc^{3+}$).

In some embodiments of the disclosed kit described above, the kit comprises a radionuclide for imaging such as technetium-99m ($^{99m}Tc^{3+}$) and a radionuclide for radiotherapy such as yttrium-90 ($^{90}Y$).

In some embodiments of the disclosed kit described above, the kit comprises a radionuclide for PET imaging and a radionuclide for radiotherapy.

In some embodiments of the disclosed kit described above, the kit comprises a radionuclide for PET imaging such as gallium-68 ($^{68}Ga$) and a radionuclide for radiotherapy such as yttrium-90 ($^{90}Y$).

In some embodiments of the disclosed kit described above, the kit comprises a radionuclide for SPECT imaging and a radionuclide for radiotherapy.

In some embodiments of the disclosed kit described above, the kit comprises a radionuclide for SPECT imaging such as technetium-99m ($^{99m}Tc^{3+}$) and a radionuclide for radiotherapy such as yttrium-90 ($^{90}Y$).

In some embodiments of the disclosed kit described above, the kit comprises a radionuclide for imaging and radiotherapy such as lutetium-177 ($^{177}Lu$).

EXAMPLES

Example 1a

Polymerization of 1,1-Bis(Triethoxysilylpropyl)-1,1-Bis (Dimethylphosphonato)Methane (Cpd 1) to Yield Central Parts Xa Cpd 1 (640.8 mg, 1 mmol, synthesized as described in Example 1, EP2572736 A1) was dissolved in 20 ml aqueous 80% ethylene glycol in a three neck round bottom flask. The reaction mixture was degassed by applying vacuum to the reaction flask and thereafter filling with nitrogen gas. This procedure was repeated three times. Thereafter the reaction mixture was stirred for 24 h at 114° C. After allowing the clear solution to cool to room temperature it was filtered through a 0.45 µm sterile filter (Pall Corporation).

Example 1a1. GPC Retention Time: 14.16 Min 0.5 mg/ml albumin (from chicken egg white) solution resulted in a size: DLS=7.0 nm & GPC peak retention time=12.52 min.

GPC retention time—Superose 12 10/300 GL, 100 mM $NH_4CO_3$, pH=7.4, flow 1 ml/min.

Example 1b: Slow Polymerization of Cpd 1 to Yield Central Parts Xb 20 ml of central parts Xa were mixed with 32 ml MilliQ water in a three neck round bottom flask. The reaction mixture was degassed by applying vacuum to the reaction flask and thereafter filling with nitrogen gas. This procedure was repeated three times. Thereafter the reaction mixture was stirred for 24 h at 114° C. Cpd 1 (5.126 g, 8 mol) was dissolved in 128 ml ethylene glycol and injected into the reaction flask using a syringe pump to a final concentration of 100 mM phosphorus. The pump injection settings were 200 µl/min, selected syringe size 50 and the injection syringe used was 50 ml. A timer was connected to the pump, so that it only injected the solution 15 min per hour. The reaction mixture was stirred and heated for 49 h at a set temperature of 122° C. The actual temperature in the reaction flask was 100° C. (when 0 ml of cpd 1 solution was added), 103° C. (after 50 ml of cpd 1 solution was added), 106° C. (after 100 ml of cpd 1 solution was added), 112° C. after all the cpd 1 solution was added). After allowing the clear solution to cool to room temperature it was filtered through a Whatman glass microfiber filter (50 mm diameter, Sigma-Aldrich) using a Watson Marlow pump at speed 5.0.

Example 1b1. GPC Retention Time: 14.02 Min

Example 1c: Polymerization of 1,1-bis(triethoxysilylpropyl)-1,1-Bis(Dimethylphosphonato)Methane (Cpd 1) to Yield Central Parts Xc Cpd 1 (48.36 g, 75 mmol, synthesized as described in Example 1, EP2572736 A1) was dissolved in 800 ml ethylene glycol and then diluted with 200 ml MilliQ water in a jacketed 2 L reactor equipped with a temperature controller (Huber ministat 240) for circulating oil. The reaction mixture was degassed by applying vacuum to the reaction flask and thereafter filling with nitrogen gas. This procedure was repeated three times. The reaction mixture was stirred and heated for 33 h at 120° C. After allowing the clear solution to cool to room temperature it was diluted to 2 L with MilliQ water. The pH was adjusted to 7.4 with 1 M Trizma base and the solution was filtered through a 0.2 µm sterile Rapid Flow filter (Nalgene).

Example 1c1. GPC Retention Time: 10.28 Min

DLS hydrodynamic diameter: 15.3 nm
0.5 mg/ml albumin (from chicken egg white) solution resulted in a size: DLS=7.0 nm & GPC peak retention time=12.52 min.
GPC retention time—Superose 12 10/300 GL, 50 mM $NH_4CO_3$, pH=7.4, flow 1 ml/min.

Example 2: Adding Peripheral Part of Poly(Ethylene Oxide)-Silanes to Central Parts X General procedure: Central parts X in aqueous 80% ethylene glycol (20 ml, 100 mM P) were placed in a three neck round bottom flask and the solution was degassed by three vacuum-nitrogen cycles. Thereafter solution was stirred and heated to 114° C. Then, a solution of the trialkoxy silane-PEG precursor of the peripheral part as specified below in the individual examples 2a-e, was added via syringe pump. The pump injection settings were 150 μl/min, selected syringe size 50 and the injection syringe used was 5 ml. The reaction mixture was stirred and heated for 6 h at 114° C.

Example 2a: Peripheral Part is Derived from 2-[Methoxy(Polyethyleneoxy)Propyl]Trimethoxysilane, 6-9 EG-Units A solution consisting of 2-[methoxy(polyethyleneoxy) propyl]trimethoxysilane (90%, 6-9 EG-units, 508 μl, 1 mmol, 656 mM) in 1016 μl 100% ethylene glycol was injected with the syringe pump, to a final concentration of 46.4 mM in the reaction mixture.

Example 2a1. GPC Retention Time (Product): 14.27 Min

Example 2b: Peripheral Part is Derived from Methoxy(Polyethyleneoxy)Propyltrimethoxysilane; 90% 9-12 EG-Units A solution of methoxy(polyethyleneoxy)propyltrimethoxysilane (90% 9-12 EG-units, 616 μl, 1 mmol, 541 mM) in 1232 μl 100% ethylene glycol was injected with the syringe pump, to a final concentration of 45.8 mM in the reaction mixture.

Example 2b1. GPC Retention Time (Product): 14.37 Min

Example 2b2. GPC Retention Time (Product): 14.65 Min

2c. Prophetic Example: Peripheral Part is Derived from Methoxy(Polyethyleneoxy)Propyltrimethoxysilane; 16 EG-Units A solution of methoxy(polyethyleneoxy)propyltrimethoxysilane; 16 EG-units (1 mmol, 38 mM) dissolved in a mixture of 26 ml ethylene glycol and 1,4 dioxane (11:15) is injected with the syringe pump to a final concentration of 21.7 mM in the reaction mixture. In this case, the reaction mixture is stirred and heated for 24 h at 114° C.

Example 2d: Peripheral Part is Derived from Methoxy(Polyethyleneoxy)Propyltrimethoxysilane; 44 EG-Units A solution of methoxy(polyethyleneoxy)propyltrimethoxysilane; 44 EG-units (2.133 g, 1 mmol, 38 mM) dissolved in a mixture of 26 ml ethylene glycol and 1,4 dioxane (11:15) was injected with the syringe pump to a final concentration of 21.7 mM in the reaction mixture. In this case, the reaction mixture was stirred and heated for 24 h at 114° C.
GPC retention time (product): 13.05 min

Example 2e: Peripheral Part is Derived from Methoxy(Polyethyleneoxy)Propyltriethoxysilane, 44 EG-Units A solution of methoxy(polyethyleneoxy)propyltriethoxysilane, 44 EG-units (2.175 g, 1 mmol, 38 mM) dissolved in a mixture of 26 ml ethylene glycol: 1,4 dioxane (11:15) was injected with a syringe pump, to a final concentration of 21.7 mM in the reaction mixture. The pump injection settings were 150 μl/min, selected syringe size 50 and the injection syringe used was 50 ml. In this case the reaction mixture was stirred and heated for 24 h at 114° C.
GPC retention time (product): 13.16 min

2f. Prophetic Example: Peripheral Part is Derived from a Combination of Methoxy(Polyethyleneoxy) Propyltrimethoxysilane; 44 EG-Units and 2-[Methoxy(Polyethyleneoxy)Propyl]Trimethoxysilane; 6-9 EG-Units Central parts X in aqueous 80% ethylene glycol (20 ml, 100 mM P) are placed in a three neck round bottom flask and the solution is degassed by applying vacuum to the reaction flask and thereafter filling with nitrogen gas. This procedure is repeated three times. Thereafter the solution is stirred and heated to a temperature of 114° C. Then, a solution of methoxy(polyethyleneoxy)propyltrimethoxysilane; 44 EG-units (2.133 g, 1 mmol, 38 mM) dissolved in a mixture of 26 ml ethylene glycol: 1,4 dioxane (11:15) is injected with a syringe pump, to a final concentration of 21.7 mM in the reaction mixture. The pump injection settings should be 150 μl/min, selected syringe size 50 and the injection syringe used is 50 ml. The reaction mixture is stirred and heated for 24 h at 114° C. Then, a solution of 2-[methoxy(polyethyleneoxy)propyl]trimethoxysilane (90% 6-9 EG-units, 254 μl, 0.5 mmol, 656 mM) in 508 μl 100% ethylene glycol is injected with a syringe pump, to a final concentration of 10.7 mM in the reaction mixture. The pump injection settings should be 150 μl/min, selected syringe size 50 and the injection syringe used is 5 ml. The reaction mixture is stirred and heated for 6 h at 114° C.

Example 3: Silica Gel Treatment of Nanostructures to Remove Peripheral Part Monomers that Adhere, but are not Covalently Bound to the Nanostructures Nanostructures from example 2b were placed in a three neck round bottom flask and the solution was degassed by three cycles of vacuum-nitrogen. Thereafter the solution was stirred and heated to a temperature of 114° C. The nitrogen gas flow was increased to create a slight outwards pressure and 250 mg of silica gel (pore size 60 Å, particle size 40-63 μm, Sigma Aldrich) was added to the three neck round bottom flask. The reaction mixture was stirred and heated for 1 h at 114° C. After allowing the clear solution to cool to room temperature it was filtered through a 0.45 μm sterile filter (Pall Corporation).
Run 1: 0.37 mmol cpd 1. 1.79 mmol PEG9-12. Expected Si/P ratio from ICP 3.39. Final Si/P ratio from ICP 1.71, indicating that 70% of added PEG was removed. Cleared 336 mol % PEG. 142% mol PEG remaining.
Run 2: 1.12 mmol cpd 1. 1.79 mmol PEG9-12. Expected Si/P ratio from ICP 1.80. Final Si/P ratio from ICP 1.45, indicating that 44% of added PEG was removed. Cleared 70 mol % PEG. 90 mol % PEG remaining.

Example 4: Ultrafiltration of Nanostructures Synthesized According to Example 2

A solution of nanostructures from example 2 was diluted with MilliQ $H_2O$ (20 ml). The pH was adjusted from pH 2 to pH 7.0-7.5 using 1M Tris base. The solution was transferred to 300 kDa spinfilters (Vivaspin® 20, Sartorius) and centrifuged at 3500 rpm and 25° C. for 30 min. The collected permeates were transferred to 50 kDa spinfilters (Millipore) and centrifuged at 3500 rpm and 25° C. for 30 min to remove free PEG-silane monomers and small crosslinked PEG-silane oligomers that had not attached to the nanostructures. Repeated addition of MilliQ water and filtration of the collected retentate was carried out. The centrifugation times after each addition were 15 min, 10 min, 5 min, 5 min and 5 min respectively.

Run 1: 1.12 mmol cpd 1. 1.80 mmol PEG9-12. Expected Si/P ratio from ICP 1.806. Final Si/P ratio from ICP 1.646, indicating that 20% of added PEG was removed. Cleared 32 mol % PEG. 129% mol PEG remaining. Yield after wash (from ICP): P: 20.7%.
GPC retention time (product): 12.82 min Run 2: 1.12 mmol cpd 1. 1.80 mmol PEG9-12. Expected Si/P ratio from ICP 1.806. Final Si/P ratio from ICP 1.634, indicating that 21% of added PEG was removed. Cleared 34 mol % PEG. 127% mol PEG remaining. Yield after wash (from ICP): P: 27.5%.
GPC retention time (product): 13.20 min

Example 4b. Ultrafiltration and Diafiltration of Solutions Containing Nanostructures 1 L of nanostructures synthesized according to example 1c was diluted with 5 L MilliQ water. The solution containing nanostructures was filtered by tangential flow filtration through a 300 kDa Centramate T-series casette (Pall) and collected on a 100 kDa Centramate T-series casette (Pall). 461: 75 mmol cpd 1. Yield after filtration (from ICP): P: 29%.
GPC retention time (product): 10.32 min
DLS hydrodynamic diameter: 12.7 nm

Example 5: Yttrium-89 Loading of Nanostructures and Purification by Ultrafiltration Yttrium chloride hexahydrate (521.8 mg, 1.72 mmol) was dissolved in 10 ml MilliQ water to a concentration of 172 mM. A solution of 10 ml ultrafiltered nanostructures according to example 4 was stirred and 600 µl of 172 mM yttrium chloride hexahydrate solution was added in 100 µl aliquots under stirring. The solution was allowed to mix at room temperature for 24 h. Thereafter the solution was transferred to 300 kDa spinfilters (Vivaspin® 20, Sartorius) and centrifuged at 3500 rpm and 25° C. for 30 min. The collected permeates were transferred to 100 kDa spinfilters (Millipore) and centrifuged at 3500 rpm and 25° C. for 30 min to remove any free yttrium ions. MilliQ water was added and filtration of the collected retentate was carried out at 3500 rpm and 25° C. for 5 min. The final volume of the retentate collected is about 5 ml.

1.12 mmol cpd 1. 1.80 mmol PEG9-12. 0.114 mmol Y. Yield after wash (ICP) P: 46.9% Y: 45.9%. Total yield P after wash in example 4 and 5: 12.9%.
GPC Peaks after Y Addition.
GPC retention time: 10.58 min (product), 18.54 min (salts)
GPC Peaks after Ultrafiltration.
GPC retention time: 10.76 min (product). Peak height at 18.54 min reduced, indicating that 99% of free yttrium ions were removed.

Example 6: Yttrium-89 Loading of Nanostructures in the Presence of Calcium Chloride and Purification by Ultrafiltration Yttrium chloride hexahydrate (521.8 mg, 1.72 mmol) was dissolved in 10 ml MilliQ water to a concentration of 172 mM. Calcium chloride (190.9 mg, 1.72 mmol) was dissolved in 10 ml MilliQ water to a concentration of 172 mM. 116 µl (19.7 µmol Ca) of 172 mM calcium chloride solution was added to a solution of 10 ml ultrafiltered nanostructures according to example 4 and the mixture was stirred and heated to 56° C. 175 µl (30.1 µmol) of 172 mM yttrium chloride hexahydrate solution was added under stirring. The solution was allowed to mix at 56° C. for 1 h. After the clear solution was allowed to cool to room temperature, it was transferred to 300 kDa spinfilters (Vivaspin® 20, Sartorius) and centrifuged at 3500 rpm and 25° C. for 30 min. The collected permeates were transferred to 100 kDa spinfilters (Millipore) and centrifuged at 3500 rpm and 25° C. for 30 min to remove any free yttrium ions. MilliQ water was added and filtration of the collected retentate was carried out at 3500 rpm and 25° C. for 5 min. The final volume of the retentate collected is about 5 ml.

Yield (compared to added starting material) after ultrafiltration (from ICP): P: 5.8%. Si: 6.2%. Y: 23.9%.
GPC Peaks after Y Addition.
GPC retention time: 11.00 min (product), 18.68 min (salts)
GPC Peaks after Ultrafiltration.
GPC retention time: 10.98 min (product), 18.57 min (salts). Peak height at 18.57 min reduced, indicating that 96% of free yttrium ions were removed.

Example 7: Other Metal Ions Loaded into Nanostructure X

Example 7a: Lutetium Loaded into Nanostructure X

A solution of nanostructures according to example 2a (18 ml, 1.22 mmol P) was diluted with 18 ml MilliQ water. Lutetium chloride hexahydrate (669.8 mg, 1.72 mmol) was dissolved in 10 ml aqueous 40% ethylene glycol to a concentration of 172 mM. Lutetium chloride solution (568 µl, 97.7 µmol) was added to the nanostructures Xb and stirred for 24 h at room temperature. pH=1.93. pH was adjusted to 7.31 with 1M Tris base. The clear solution was transferred to 300 kDa spinfilters (Vivaspin® 20, Sartorius) and centrifuged at 3500 rpm and 25° C. for 30 min. The collected permeates were transferred to 100 kDa spinfilters (Millipore) and centrifuged at 3500 rpm and 25° C. for 30 min to remove any free lutetium ions. Repeated addition of MilliQ water and filtration of the collected retentate was carried out. The centrifugation times after each addition were 5 min, 5 min, 3 min, 3 min and 3 min respectively. The final volume of the retentate collected was about 6 ml.
Composition (ICP, mole ratio): P/Lu=7.04, P/Si=1.53, Si/Lu=10.79. Yield (%): P=17.1, Lu=29.6.
GPC retention time: 11.42 min (product), 18.69 min (salts).

Example 7b: Uranium Loaded into Nanostructure X

A solution of nanostructures according to example 2b (72 ml, 5.53 mmol P) was diluted with 72 ml MilliQ water (pH=2.32). 6 ml of this solution was stirred with 2 wt % uranyl acetate (21.8 µmol) at room temperature for 18 h. The solution was diluted with 6 ml MilliQ water. The clear solution was transferred to 300 kDa spinfilters (Vivaspin® 20, Sartorius) and centrifuged at 3500 rpm and 25° C. for 30 min. The collected permeates were transferred to 50 kDa spinfilters (Millipore) and centrifuged at 3500 rpm and 25° C. for 30 min to remove any free uranium ions. Repeated addition of MilliQ water and filtration of the collected retentate was carried out. The centrifugation times after each addition were 15 min, 10 min, 5, 5 m 5 min and 5 min respectively. The final volume of the retentate collected was 7 ml.
GPC retention time: 13.11 min (product)

Example 7c: Barium Loaded into Nanostructure X

A solution of nanostructures Xa according to example 2a (20 ml, 2 mmol P) was pH adjusted to 5.15 with 1M Tris base. The solution was placed in a reaction flask and degassed by applying vacuum to the reaction flask and thereafter filling with nitrogen gas. This procedure was repeated three times. Barium nitrate (38.4 mg, 146.9 µmol) was dissolved in 0.847 ml aqueous 40% ethylene glycol to a concentration of 173 mM. Barium nitrate solution (847 µl, 146.9 µmol) was added to the nanostructures Xa and stirred for 112 h at room temperature. Thereafter the solution was heated to 100° C. and a solution of the crosslinker tetraethylorthosilicate (669 µl, 3.0 mmol) in 1831 µl of a mixture of ethylene glycol:99.5% ethanol (4 mol:5 mol) was injected with a syringe pump. A timer was connected to the pump, so that it only injected the solution 15 min per 2 hours. The pump injection settings were 150 µl/min, selected syringe size 100 and the injection syringe used was 2 ml. The reaction mixture was stirred and heated for 48 h at 100° C., followed by 24 h at 114° C. After cooling to room temperature, the clear solution was diluted with 25 ml MilliQ water. pH=3.44. The pH was adjusted to 7.06 with 1M Tris base. The solution was transferred to 100 kDa spinfilters (Millipore) and centrifuged at 3500 rpm and 25° C. for 60 min. The collected permeates were transferred to 10 kDa spinfilters (Millipore) and centrifuged at 3500 rpm and 25° C. for 30 min to remove the free barium ions. Repeated addition of MilliQ water and filtration of the collected retentate was carried out. The centrifugation times after each addition were 30 min, 30 min, 15 min, 15 min and 15 min respectively. The final volume of the retentate collected was 17 ml.
Composition (ICP, mole ratio): Si/P=1.42, P/Ba=10.67, Si/Ba=15.12.
GPC retention time: 14.26 min (product)

Example 7d: Gallium Loaded into Central Part Xc

A solution of nanostructures according to example 1c (5 ml, 0.324 mmol P) was diluted with MilliQ water to 64.74 mM P. Gallium standard (1000 mg/L, Fluka) was dissolved in MilliQ water to a concentration of 3.2 mM. Gallium solution (920 µl, 13.2 µmol) was added to the central parts Xc and stirred for 1 h at room temperature. The pH was adjusted to 7.4 with 1 M Tris base. The clear solution was transferred to 10 kDa spinfilters (Vivaspin® 20, Sartorius) and centrifuged at 3500 rpm and 25° C. for 15 min. MilliQ water was added to the retentate and filtration of the collected retentate was carried out. The centrifugation times after was 15 min. The final volume of the retentate collected was about 3 ml.
Composition (ICP, mole ratio): P/Ga=27.47, P/Si=0.926, Si/Ga=29.67
Yield (%): P=100%, Ga=80%.
GPC retention time: 10.23 min (product), 19.17 min (salts).

Example 8a: Stability Measurement for Yttrium-89 Containing Nanostructures

Yttrium-containing nanostructures were diluted with MilliQ water to a concentration of 1 mM yttrium. 150 µl nanostructure solution was mixed with 150 µl 1 mM EDTA 50 mM Tris-HCl pH 7.5 and allowed to stand at room temperature for 1 h. 100 µl of the mixture was removed and labelled XXX-pre. The remaining 200 µl solution was placed into an 0.5 ml Amicon 10 kDa spin filter and centrifuged for 10 min at 13.4 krpm. 100 µl of permeate was removed and labelled XXX-post. Yttrium concentrations in samples xxx-pre and xxx-post were determined by ICP-AES. Yttrium stability was calculated using the equation below, where the calculated stability refers to the % of yttrium remaining in the nanostructures after EDTA-treatment.

$$\text{Yttrium stablility (\%)} = 100 - \left(\frac{[Y]_{xxx-post}}{[Y]_{xxx-pre}} \times 100\right)$$

Nanostructures according to Xb-2a. Yttrium stability 94.6%.
Nanostructures according to Xc. Yttrium stability 98.85±0.75%.

Example 8b: Stability Measurement for Gallium Containing Nanostructures

The procedure for stability measurement was the same as in example 8a. Nanostructures according to Xc. Gallium stability 91.9±2.8%.

Example 9: Characterization of Nanostructures According to Examples 1, 2, 4, 5, 7

TABLE 2

| Nanostructure ID | Central part (mM P) | Peripheral part (mol PEG/mol cpd 1•100%) | Chelated ion | pH | Osmolality (mOs/kg) | Hydrodynamic diameter (nm) |
|---|---|---|---|---|---|---|
| Xb-2a-1 | 10.8 | 92 | 2 mM Y | 7.7 | 315 | 14 |
| Xb-2a-2 | 18.6 | 90 | 2 mM Y | 7.37 | 328 | 14 |
| Xb-2a-3 | 14 | 106 | 2 mM Lu | 7.3 | 449 | 9 |
| Xb-2b-1 | 16.6 | 116 | 2 mM Y | 7.6 | 341 | 20 |
| Xb-2b-2 | 17.4 | 52 | 2 mM Y | 7.37 | 321 | 17 |
| Xb-2b-3 | 10.6 | 90 | 2 mM Y | 7.44 | 346 | 21 |
| Xb-2b-4 | 10 | 130 | none | 7.3 | 477 | 8 |
| Xb-1 | 18.2 | 0 | 2 mM Y | 7.5 | 445 | 22 |
| Xb-2e-1 | 22.4 | 100 | 4 mM Y | 7.36 | 320 | 22 |

TABLE 2-continued

| Nanostructure ID | Central part (mM P) | Peripheral part (mol PEG/mol cpd 1•100%) | Chelated ion | pH | Osmolality (mOs/kg) | Hydrodynamic diameter (nm) |
|---|---|---|---|---|---|---|
| Xc | 55.4 | 0 | 2.4 mM Y | 7.29 | NA | 12.0 |
| Xc | 118.3 | 0 | 4.3 mM Ga | 7.43 | NA | 12.8 |

Notes
0.5 mg/ml albumin (from chicken egg white) solution resulted in a size: DLS = 7.0 nm (albumin in 150 mM NaCl, hydrodynamic diameter obtained from volume psd) & GPC peak retention time = 12.52 min. Nanostructures' hydrodynamic diameter obtained from GPC retention times calibrated according to protein standards.
Mol % PEG taken from ICP Si/P ratio (Mol % PEG = (Si/P ratio-1)•2•100%)

Example 10: Viscosity

A solution of nanostructures Xb with a peripheral part according to example 2b were loaded with 5.9 mM yttrium, with a loading of 10 P/Y. The viscosity was measured in a capillary viscosimeter. The measured viscosity of yttrium-loaded nanostructures was 1.603±0.070 mPa·s.

Figure 9:
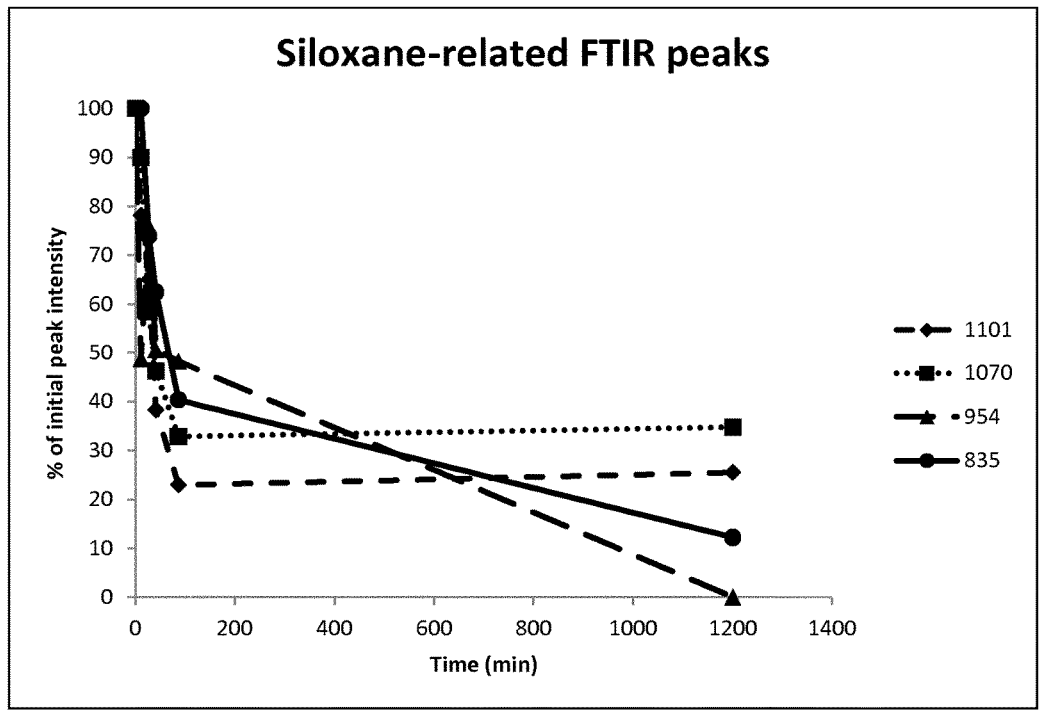
FIG. 9 shows siloxane-related FTIR peaks and the change in peak intensity vs. heating time at 114° C.

Example 11: Evidence of Crosslinking of Cpd 1 to Form Naked Nanostructures and of Chemical Modification of PEG-Silane Peripheral Part Upon Heating Example 11a: FTIR Indicates Chemical Modification of Cpd 1 Upon Heating Cpd 1 in 80% aqueous ethylene glycol was heated at 114° C. for 20 h as in example 1a and analyzed at several time points by Fourier Transform Infrared Spectroscopy. FTIR peaks were normalized to give equal peak height of the peak at 898 $cm^{-1}$ (C—C hydrocarbon skeletal vibrations). Relevant peak wavenumbers for siloxane groups were 1101 $cm^{-1}$ (Si—OEt), 1070 $cm^{-1}$ (Si—OEt), 954 $cm^{-1}$ (Si—OEt) and 835 $cm^{-1}$ (Si—OH). Decrease in peak intensity of all these peaks over time was observed, indicating that the number of ethoxysilane groups and the number of hydroxylsilane groups decreases, which is consistent with crosslinking of cpd 1 to form a crosslinked polymer network. After completed crosslinking, 25-35% unreacted ethoxysilane groups remain, as well as a small fraction of hydroxysilanes, corresponding to a degree of crosslinking of 390-450%. See FIG. 9.

Figure 10:
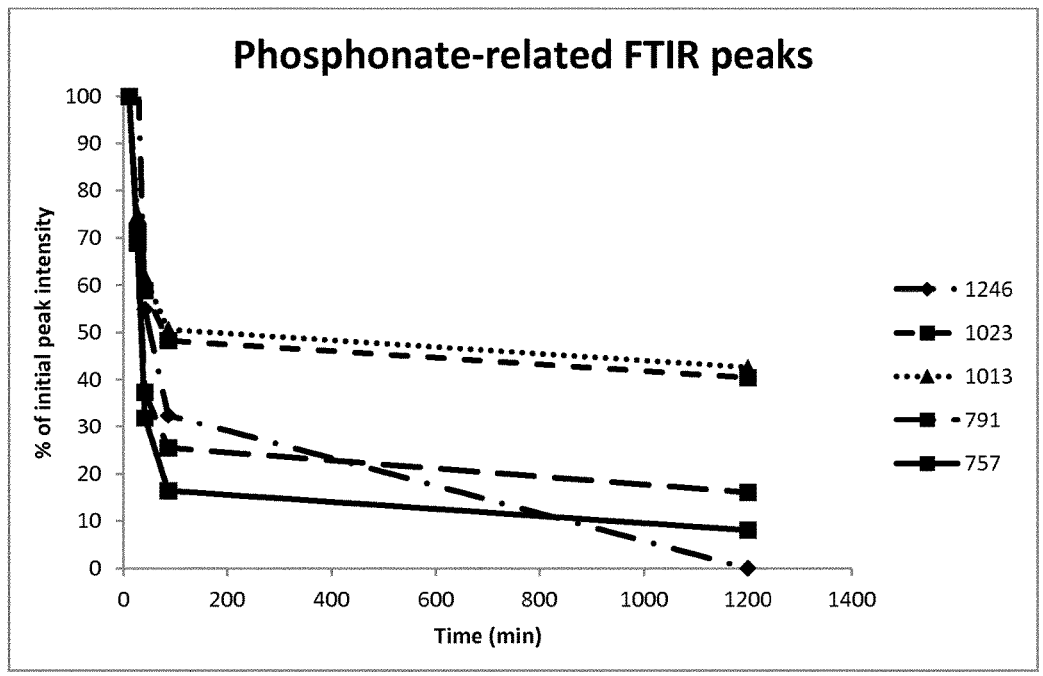
FIG. 10 shows phosphonate-related FTIR peaks and the change in peak intensity vs. heating time at 114° C.

Relevant peak wavenumbers for phosphonate groups were 1246 $cm^{-1}$ (R—P=O(OCH$_3$)$_2$ P—O vibration), 1023 $cm^{-1}$ (P—OMe), 1013 $cm^{-1}$ (P—OH), 791 $cm^{-1}$ (P—OMe) and 757 $cm^{-1}$ (P—OMe). Decrease in peak intensity of all these peaks over time was observed, indicating that the number of methoxyphosphonate groups decreases. The peak at 1013 $cm^{-1}$ overlapped with silane peaks, and thus indicated the presence of hydroxyphosphonate groups, but they were not possible to quantify. After completed crosslinking, 10-50% unreacted methoxyphosphonate groups remain. See FIG. 10.

Figure 11:
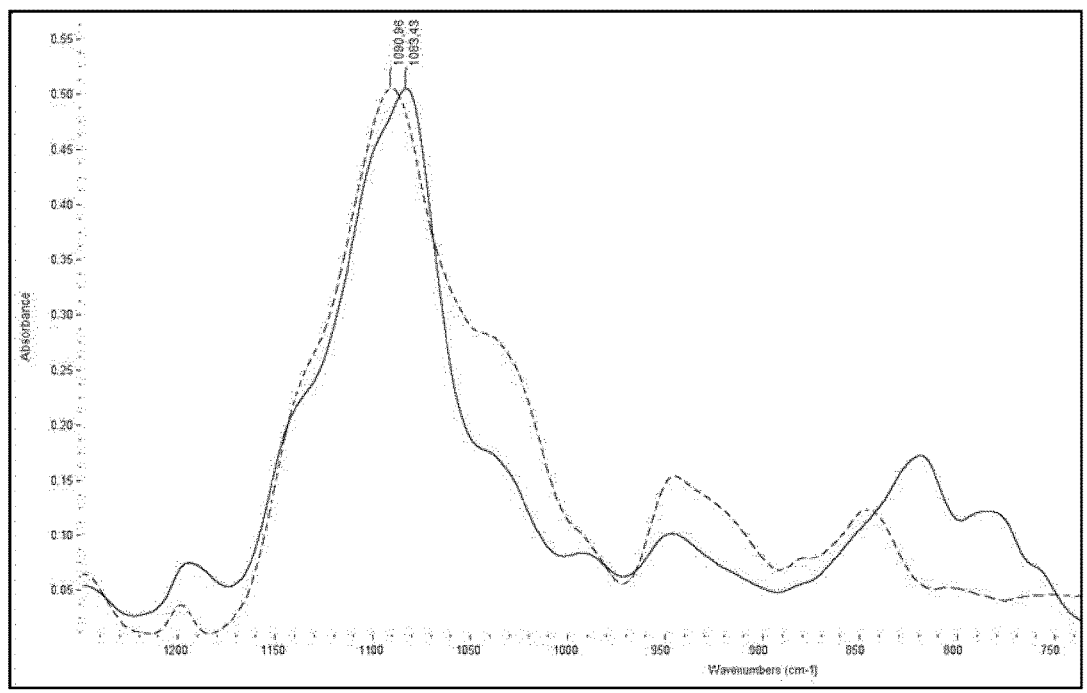
FIG. 11 shows FTIR spectra of PEG-silane (9-12) monomer (black line) and heated PEG-silane (9-12) monomer (broken black line).
Figure 12:
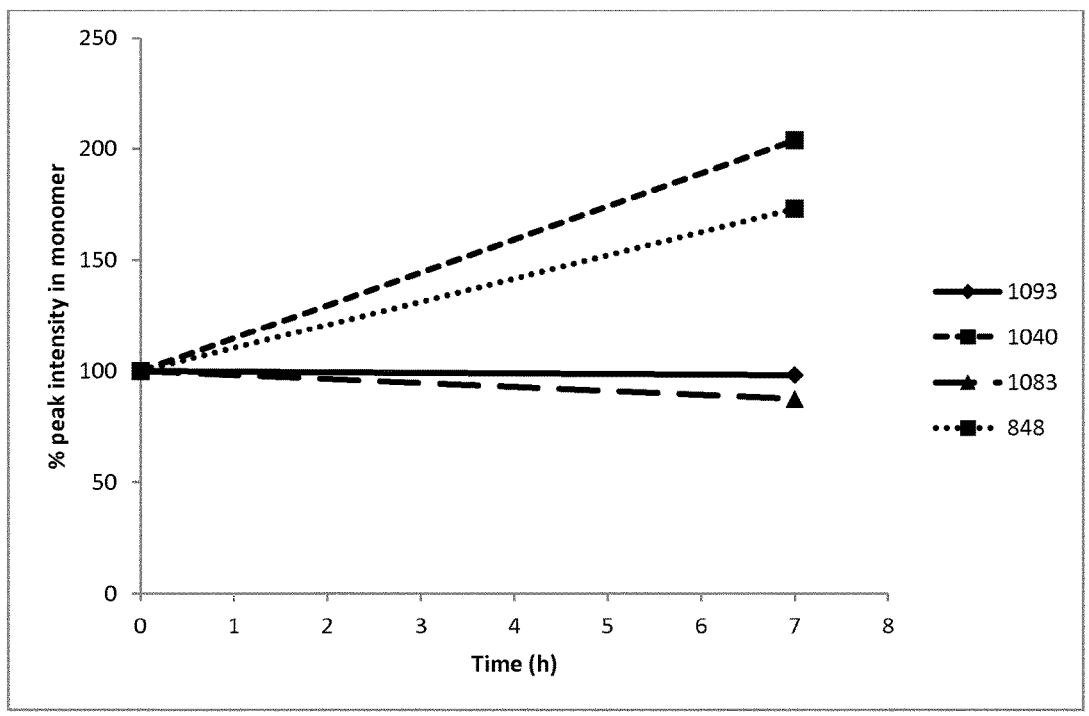
FIG. 12 shows normalized peak intensities after 7 h of heating the PEG-silane monomer. They are normalized to give same peak intensity for 2868 cm$^{-1}$ (attributed to symmetric CH$_2$ stretch).

Example 11b: FTIR Indicates Chemical Modification of PEG-Silane Monomer Upon Heating FTIR spectra of PEG-silane monomers 2-[Methoxy(polyethyleneoxy)propyl]trimethoxysilane; 90% 6-9 EG-units (PEG6-9) and methoxy(polyethyleneoxy)propyltrimethoxysilane; 90% 9-12 EG-units (PEG9-12) were compared with FTIR spectra of PEG-silane monomers in aqueous 80% ethylene glycol heated at 114° C. for 7 h. FTIR spectra showed that chemically, the substances differed in peaks at wavenumbers 1093 $cm^{-1}$ (Si—O—Si), 1083 $cm^{-1}$ (Si—O—CH$_3$), 1040 $cm^{-1}$ (Si—O—Si) and 848 $cm^{-1}$ (Si—OH). When PEG-silane monomers were heated, peaks appeared at 1093 $cm^{-1}$ and 1040 $cm^{-1}$, indicating the presence of open chain siloxane Si—O—Si groups. The appearance of the peak at 848 $cm^{-1}$ in heated PEG-silane monomers indicates the presence of Si—OH groups, whereas the disappearance of the peak at 1083 $cm^{-1}$ in after heating indicates loss of Si—OCH$_3$ methoxysilane groups in the PEG-silane monomer. This disappearance of Si—OCH$_3$ methoxysilane groups and appearance of Si—O—Si groups is what is expected from a PEG-silane forming a covalent bond to the central part. See FIG. 11 and FIG. 12

Example 12: TEM Imaging of Nanostructures X Loaded with Uranium

Figure 13:
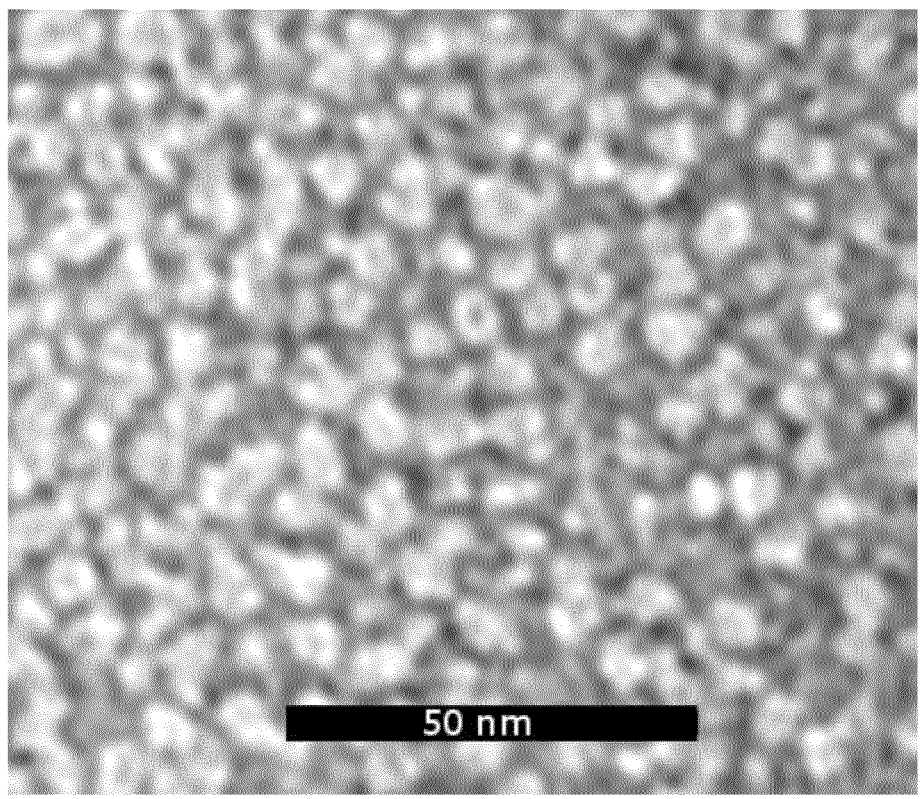
FIG. 13 is a TEM image of nanostructures coated with 130 mol % PEG9-12 and filled with uranyl acetate by stirring empty coated nanoparticles with uranyl acetate at room temperature for 24 h. Nanostructure concentration 29.2 mM P. Loading with uranyl at a ratio of 10 P/U.

The nanostructures were diluted 30× with MilliQ water and 3 µl of sample was applied on a carbon 400 mesh copper grid that has been subjected to glow discharging. Samples were negatively stained with UAR-EMS. Subsequently, the grids were washed with ultrapure water and imaged using an FEI Tecnai 10 electron microscope run at 100 keV accelerating voltage. Images were acquired using a 2 k×2 k Veleta CCD camera (Olympus Soft Imaging System). Several globular nanostructures with a diameter larger than 8 nm were observed. The nanostructures contain a central part (dark core) and a peripheral part (white ring). See FIG. 13

Example 13: In Vivo: Pharmacokinetic Study in a Mouse Model

Nanostructure X solutions were administered intravenously* at 20 µmol Y/kg or 20 µmol Lu/kg and 10 ml/kg during 5 s to mice (N=2/test item). After administration the animals were subjected to blood sampling. Upon termination of the experiment, the kidneys and livers were collected. Injected nanostructure solutions, plasma samples and digested tissue samples were analyzed by ICP-AES for yttrium or lutetium and silicon content.

TABLE 3

| Substance ID | Peripheral part (mol PEG/mol cpd 1•100%) | Chelated ion | Time after injection (h) | % injected ion dose in plasma | % injected Si dose in plasma | % injected ion dose in liver | % injected Si dose in liver |
|---|---|---|---|---|---|---|---|
| Xb-2a-1 | 92 | Y | 1 | 44.2 ± 11.2 | 61.4 ± 16.0 | | |
| | | | 6 | 7.5 ± 1.4 | 11.9 ± 2.3 | 45.3 ± 10.0 | 30.9 ± 8.5 |
| Xb-2a-2 | 90 | Y | 1 | 46.1 ± 2.3 | 83.9 ± 7.4 | | |
| | | | 6 | 20.4 ± 3.0 | 31.3 ± 4.8 | 28.0 ± 2.0 | 21.9 ± 2.5 |
| Xb-2a-3 | 106 | Lu | 1 | 170.2 ± 1.6** | 110.2 ± 15.5** | | |
| | | | 6 | 60.3 ± 8.4 | 39.8 ± 4.8 | 23.3 ± 1.2 | 14.0 ± 2.7 |
| Xb-2b-1 | 116 | Y | 1 | 43.6 ± 4.9 | 69.2 ± 7.0 | | |
| | | | 6 | 23.4 ± 0.6 | 33.0 ± 0.5 | 15.7 ± 0.9 | 9.2 ± 1.2 |
| Xb-2b-2 | 52 | Y | 1 | 55.4 ± 3.7 | 94.9 ± 7.8 | | |
| | | | 6 | 22.9 ± 0.0 | 35.6 ± 0.6 | 36.6 ± 6.2 | 30.2 ± 5.5 |
| Xb-2b-3 | 90 | Y | 1 | 110.7 ± 18.5** | 75.3 ± 12.0 | | |
| | | | 6 | 53.1 ± 6.7 | 36.5 ± 3.7 | 20.2 ± 3.6 | 6.6 ± 1.6 |
| Xb-2b-4 | 130 | none | 1 | | 58.0 ± 0.0 | | |
| | | | 6 | | 25.1 ± 1.0 | | 2.5 ± 0.1 |
| Xb-1 | 0 | Y | 1 | 8.9 ± 0.6 | 4.7 ± 1.0 | | |
| | | | 6 | 1.5 ± 0.1 | 1.4 ± 2.0 | 88.2 ± 12.1 | 77.1 ± 6.0 |

*The solutions were formulated to be neutral (pH 7.4), electrolyte balanced (1.4 eq. CaCl$_2$ added/eq. Y, and isoosmotic (mannitol added) with blood.
**% Injected dose exceeds 100% due to experimental uncertainty The negative control example, containing nanostructures lacking a peripheral part, shows the importance of the peripheral part for obtaining long circulation time in blood.

TABLE 4

| Substance ID | Peripheral part (mol PEG/mol cpd 1•100%) | Chelated ion | Time after injection (h) | % injected ion dose in kidneys | % injected Si dose in kidneys |
|---|---|---|---|---|---|
| Xb-2a-3 | 106 | Lu | 6 | 1.6 ± 0.2 | 0.4 ± 0.5 |
| Xb-2b-3 | 90 | Y | 6 | 1.6 ± 0.1 | 0.7 ± 0.3 |
| Xb-2b-1 | 116 | Y | 6 | 1.7 ± 0.1 | 2.0 ± 1.9 |
| Xb-2b-4 | 130 | none | 6 | | 0.0 ± 0.0 |

*The solutions were formulated to be neutral (pH 7.4), electrolyte balanced (1.4 eq. CaCl$_2$ added/eq. Y, and isoosmotic (mannitol added) with blood.

Only a small fraction of nanostructures X distributed to the kidneys.

Example 14: Excretion Study in a Rat Model

The excretion pattern of nanostructure X solutions after intravenous injection in rat was investigated. Nanostructure solution was administered intravenously at 10 µmol Y/kg and 3.3 ml/kg during 20 s. The rats were then put into separate metabolic cages for 24 h (N=3) or 72 h (N=3). Two animals were used as control animals and were not administered. Urine and faeces were collected every 24 h throughout the study. After end of urine and faeces sampling, the urine remaining in the bladder and the faeces remaining in the colon and intestine were collected. The injected nanostructure solution was analyzed by ICP-AES for yttrium, silicon and phosphorus content. Urine and faeces samples were analyzed by ICP-AES for yttrium and silicon content.

TABLE 5

| Substance ID | Peripheral part (mol PEG/mol cpd 1•100%) | Chelated ion | Time after injection (h) | % injected Y dose in faeces | % injected Y dose in urine |
|---|---|---|---|---|---|
| Xb-2b-3 | 86 | Y | 24 | 3.3 ± 2.0 | 1.3 ± 0.6 |
| | | | 72 | 12.9 ± 3.7 | 2.2 ± 1.0 |

Nanostructures X were mainly excreted via faeces, with minimal excretion via urine.

15. Prophetic Example. Radioactive Loading of Nanostructures with Actinium-225 ($^{225}$Ac), Copper-62 ($^{62}$Cu), Copper-64 ($^{64}$Cu), Copper-67 ($^{67}$Cu), Gallium-67 ($^{67}$Ga), Gallium-68 ($^{68}$Ga), Holmium-166 ($^{166}$Ho), Indium-111 ($^{111}$In), Lead-212 ($^{212}$Pb), Lutetium-177 ($^{177}$Lu), Radium-223 ($^{223}$Ra), Rhenium-186 ($^{186}$Re), Rhenium-188 ($^{188}$Re), Rubidium-82 ($^{82}$Rb), Samarium-153 ($^{153}$Sm), Strontium-89 ($^{89}$Sr), Technetium-99m ($^{99m}$Tc$^{3+}$), Thallium-201 ($^{201}$Tl), Thorium-227 ($^{227}$Th), Yttrium-86 ($^{86}$Y), Yttrium-90 ($^{90}$Y) or Zirconium-89 ($^{89}$Zr)

Prepare 20 ml of empty nanostructures Xb (starting material 2 mmol P) with peripheral part according to example 2b, ultrafiltered according to example 5 between 300 kDa and 50 kDa and pH adjusted to 7.0-7.5 with 1M Tris base. Dilute nanostructure solutions to 20 mM P. Prepare 0.4 µM cationic yttrium-90 solution in water by dissolving 143.8 ng yttrium-90 in 4 ml MilliQ water. Prepare 0.4 µM cationic lutetium-177 solution in water by dissolving 283.2 ng lutetium-177 in 4 ml MilliQ water (or 0.4 µM cationic actinium-225 ($^{225}$Ac), copper-62 ($^{62}$Cu), copper-64 ($^{64}$Cu), copper-67 ($^{67}$Cu), gallium-67 ($^{67}$Ga), gallium-68 ($^{68}$Ga), holmium-166 ($^{166}$Ho), indium-111 ($^{111}$In), lead-212 ($^{212}$Pb), radium-223 ($^{223}$Ra), rhenium-186 ($^{186}$Re), rhenium-188 ($^{188}$Re), rubidium-82 ($^{82}$Rb), samarium-153 ($^{153}$Sm), strontium-89 ($^{89}$Sr), technetium-99m ($^{99m}$Tc$^{3+}$), thallium-201 ($^{201}$Tl), thorium-227 ($^{227}$Th), yttrium-86 ($^{86}$Y), or zirconium-89 ($^{89}$Zr)).

Prepare mixed nanostructure+radionuclide solutions 1 and 2 by mixing 4 ml of empty nanostructures (20 mM P) with 4 ml of radionuclide solution (0.4 µM) at room temperature or at 50° C. respectively for 1 h using a magnetic stirring bar.

Thus the mixed solutions will contain 10 mM P and 0.2 µM radionuclide (50000 P/radionuclide).

Filter each solution as follows: After 1 h, filter the nanostructures with a 300 kDa spinfilter (Vivaspin® 20, Sartorius) centrifuged at 3500 rpm and 25° C. for 30 min. Transfer the permeate to a 10 kDa spinfilter (Millipore) and centrifuge at 3500 and 25° C. for 30 min. Carry out repeated addition of MilliQ water and filtration of the collected retentate. The centrifugation times after each addition are 10 min, 10 min, and 10 min respectively. Dilute the remaining retentate with MilliQ water to 4 ml.

16. Prophetic Example. Stability Measurement for Actinium-225 ($^{225}$Ac), Copper-62 ($^{62}$Cu), Copper-64 ($^{64}$Cu), Copper-67 ($^{67}$Cu), Gallium-67 ($^{67}$Ga), Gallium-68 ($^{68}$Ga), Holmium-166 ($^{166}$Ho), Indium-111 ($^{111}$In), Lead-212 ($^{212}$Pb), Lutetium-177 ($^{177}$Lu), Radium-223 ($^{223}$Ra), Rhenium-186 ($^{186}$Re), Rhenium-188 ($^{188}$Re), Rubidium-82 ($^{82}$Rb), Samarium-153 ($^{153}$Sm), Strontium-89 ($^{89}$Sr), Technetium-99m ($^{99m}$Tc$^{3+}$), Thallium-201 ($^{201}$Tl), Thorium-227 ($^{227}$Th), Yttrium-86 ($^{86}$Y), Yttrium-90 ($^{90}$Y) or Zirconium-89 ($^{89}$Zr)-Containing Nanostructures For each nanostructure X/radionuclide solution according to example 15, mix 250 µl solution with 250 µl MilliQ water or rat blood plasma and incubate for 6 h or 24 h at room temperature (4 samples per solution from example 15). After incubation, remove 100 µl of the mixture for each sample and label xxx-pre. Place 200 µl solution in an 0.5 ml Amicon 10 kDa spinfilter and centrifuge for 10 min at 13.4 krpm. Remove 100 µl of the permeate and label xxx-post. Measure α-radiation, β-radiation or γ-radiation in xxx-pre and xxx-post. Calculate the radionuclide stability (% of radionuclide remaining in the nanostructures after filtration) using the equation below.

$$\text{Radionuclide stablility (\%)} = 100 - \left( \frac{[\text{Radionuclide}]_{xxx-post}}{[\text{Radionuclide}]_{xxx-pre}} \times 100 \right)$$

17. Prophetic Example. Treatment of Solid Tumors Using $^{90}$Y-Loaded Nanostructures Therapy with radionuclides is performed in facilities capable of meeting the standards for treatment with unsealed radioactive sources and licensed according to the national regulations. The personnel engaged in the preparation and administration procedures should have the required qualification and the appropriate authorization for the use of radionuclides. All disposable equipment used for preparing and administering radionuclides should be disposed of as radioactive waste and remaining radionuclide is returned to an authorized recipient of radioactive decay.

Preparation of Radioloaded Nanostructures:

Personnel preparing the nanostructures should wear plastic gloves, disposable waterproof gowns, and eye protection. Preparatory procedures are performed using at least 1 cm-thick perspex or lead-loaded perspex shields using forceps and tongs as gripping tools. The nanostructures are supplied as a kit containing the non-radioactive components required for generating a single dose of $^{90}$Y-loaded nanostructures as well as a formulated buffer solution in a bottle and an empty reaction vial. The radioactive component, carrier-free pharmaceutical grade $^{90}$Y, is obtained separately upon order from the manufacturer. The carrier-free $^{90}$Y is added to the nanostructures and the buffer in the provided empty reaction vial according to the detailed instructions provided with the kit. Aseptic techniques are used at all stages of preparation. After loading, the nanostructures are stored at 2-8° C. and administered within 8 hours.

Administration:

Before administering the radioloaded nanostructures, the activity of the solution for administration is measured. $^{90}$Y-loaded nanostructures are administered as an intravenous infusion either directly through a three-way valve line or using a shielded remote infusion system. A line filter is used. After infusion, the line is flushed with at least 10 ml of sodium chloride (0.9%) solution, to ensure administration of the full dose of radiopharmaceutical agent. The patient is discharged after completion of the infusion and an adequate period of observation for side effects (20-30 minutes). Due to the short half-life of the radionuclide injected, the patient can be released shortly after administration without posing a significant risk to those around them.

18. Prophetic Example. Diagnostic Imaging of Solid Tumors Using $^{99m}$Tc$^{3+}$-Loaded Nanostructures Preparation and administration of $^{99m}$Tc$^{3+}$-loaded nanostructures supplied as a kit for gamma imaging is performed in an aseptic manner similar to the preparation and administration of $^{90}$Y-loaded nanostructures for radiotherapy. However, certain precautions and regulations are adapted to patient and personnel safety guidelines when handling gamma-emitting radionuclides. Prepared $^{99m}$Tc$^{3+}$-loaded nanostructures are injected as a venous catheter infusion followed by a flush with normal saline. Imaging is performed after 1-12 hours following injection.

Example 19: In-Vivo Experiment, Localization of Y to Tumor

Nanostructures according to example Xb-2b were administered intravenously at 10 µmol Y/kg* and 2.5 ml/kg to mice (N=3) which had previously been inoculated with the immortalized tumor cell line PC-3. The tumors were about 7 mm in diameter. After 24 h the animals were killed and the tumors were collected. Injection test items were analyzed by ICP-AES for yttrium, silicon and phosphorus content. Digested tumor samples were analyzed by ICP-AES for yttrium and silicon content. A fraction of 0.8% of the injected dose of Y was found in the tumor after 24 h.

*The solutions were formulated to be neutral (pH 7.4), electrolyte balanced (1.4 eq. CaCl$_2$ added/eq. Y, and isoosmotic (mannitol added) with blood.

20. Prophetic Example. Preparation of a Nanostructure with a Branched Central Part Based on Polyethyleimine, with DOTA as Chelating Group and Poly(Ethylene Glycol) as Peripheral Part m-PEG-COOH (average Mw 5000 g/mol, about 100 monomer units, 100 mg, 20 µmol) is dissolved in water (2 ml) whereafter N-hydroxysulfosuccinimide sodium salt (Mw 217 g/mol, 10 mg, 46 µmol) and N-(3-dimethylaminopropyl)-N'-ethylcarbodiimide hydrochloride (Mw 192 g/mol, 10 mg, 52 µmol) are added. The reaction mixture is left to stir for 2 days. Polyethyleneimine is then added to this solution (50% by weight in water, Mw 300 000, hydrodynamic diameter measured to 34 nm at pH 7, corresponds to a "surface area" of 3631 nm$^2$ for one nanostructure, so for a coverage of 1 PEG/nm$^2$, 5 nmol (=1.5 mg) of PEI is required). The reaction mixture is left to stir for 2 days. DOTA-mono-NHS-tris(t-Bu ester)HPF$_6$ salt (Macrocyclics, USA, Mw 815, 0.8 mg, 1 µmol) is added and the mixture is stirred for another 2 days. The zeta potential of the material is measured and if desired small amounts of succinic anhydride are added until the zeta potential is close to zero.

Example 21: Binding of Radioactive $^{90}$Y to Nanostructures According to Example 2a The yttrium-90 was delivered as 150 μL of an aqueous solution and to reach acceptable levels of radioactivity, this solution was diluted with 400 mL 0.4 μM yttrium-89 in water. This dilution was believed to be not interfering with the experimental outcome. Of this solution 4 mL solution was mixed with 4 mL of ta solution of nanostructures according to example 2b, at a concentration of 20 mM phosphorus. This was done twice, one mixture was subsequently stirred at room temperature (r.t.) for 1 hour (solution 1) and the other at 50° C. for 1 hour (solution 2). For both solutions, the beta radiation was measured. For this, a 100 μL aliquot was taken and diluted to 20 mL to get appropriate levels of radiation for reliable measurements. The results are shown in Table 6.

TABLE 6

The beta radiation of the mixed solutions

| Solution | Activity |
| --- | --- |
| Solution 1 | $3.19 \times 10^5$ cpm |
| Solution 2 | $3.32 \times 10^5$ cpm |

Both solutions were filtered using 15 mL 10 kDa spinfilters. Due to practical limitations, the solutions were filtered at 1000 g for 1 hour, the permeate was removed and the retentate was diluted to 15 mL and another filtration was done. This filtration was also carried out at 1000 g and was judged complete after 20 minutes. This last wash and filtration step was repeated three times. After filtration, the remaining solution was diluted to 4 mL and a 100 μL aliquot was taken up again, diluted to 20 mL and the beta radiation was measured. The measured activities are shown in Table 7.

TABLE 7

The beta radiation after filtration

| Solution | Activity | Corrected activity |
| --- | --- | --- |
| Solution 1 | $5.05 \times 10^5$ cpm | $2.59 \times 10^5$ cpm |
| Solution 2 | $5.99 \times 10^5$ cpm | $3.04 \times 10^5$ cpm |

The solutions were twice as concentrated as the ones in Table 6, so to compare the activity was divided by two. The measurement of solution 1 was performed 128 minutes later than the one in Table 6, so with the fast decay of yttrium-90 the number should be corrected to $2.59 \times 10^5$ cpm. This is 81.2% of the original solution. The measurement of solution 2 was performed 88 minutes later than the original in Table 1, and the corrected activity here is $3.04 \times 10^5$ cpm. This is 91.3% of the original solution. A blank was also measured, which was 55.1 cpm and therefore judged negligible.

The following day, 8 mixtures were made by adding 250 μL of solution 1 or 2 to 250 μL water or human plasma. These mixtures were then incubated for 6 h or 24 h and labeled as shown in table 8.

TABLE 8

Different prepared solutions of yttrium-90 and nanoparticles

| Solution no. | Mixing temp. | Solvent | Incubation (h) |
| --- | --- | --- | --- |
| 1a | r.t. | water | 6 |
| 1b | r.t. | water | 24 |
| 1c | r.t. | Human plasma | 6 |
| 1d | r.t. | Human plasma | 24 |
| 2a | 50° C. | water | 6 |
| 2b | 50° C. | water | 24 |
| 2c | 50° C. | Human plasma | 6 |
| 2d | 50° C. | Human plasma | 24 |

After incubation, 100 μL was removed and diluted to 20 mL to get a sample for pre-filtration measurement. 300 μL of the mixture was filtered through a 0.5 mL Amicon 10 kDa spinfilter. 100 μL of the filtrate was also taken up and diluted to 20 mL to get a post-filtration sample. All samples were measured and the results are shown in table 9. The radioisotope stability of each solution could then be calculated and is also given.

TABLE 9

Before and after filtration measurements of radiation, and following stability

| Solution no. | Pre-filtration activity (cpm) | Post-filtration activity (cpm) | Post-filtration blank (cpm) | Radioisotope stability (%) |
| --- | --- | --- | --- | --- |
| 1a | $1.06 \times 10^5$ | 87.3 | 22.2 | >99.9 |
| 1b | $1.47 \times 10^5$ | 97.4 | 42.3 | >99.9 |
| 1c | $1.42 \times 10^5$ | 60.7 | 5.6 | >99.9 |
| 1d | $1.38 \times 10^5$ | 63.3 | 8.2 | >99.9 |
| 2a | $1.72 \times 10^5$ | 804 | 749 | 99.6 |
| 2b | $1.69 \times 10^5$ | 90.3 | 35.2 | >99.9 |
| 2c | $1.57 \times 10^5$ | 57.1 | 2.0 | >99.9 |
| 2d | $1.55 \times 10^5$ | 60.0 | 4.9 | >99.9 |

As shown in Table 9, the difference between the post and pre-filtration samples is remarkably large. The calculated radioisotope stability is close to 100% in almost all cases. The pre- and post filtration samples were measured within one hour from each other and are not decay adjusted. Only for solution 2a, some significant activity was measured in the post-filtration sample; there is no explanation for this anomaly and it seems a measurement error. However, even this exception gives a radioisotope stability of 99.6%.

Radioisotope yttrium-90 was obtained as yttrium (III) chloride in 0.05 M HCl from Perkin Elmer. The specific activity was 500 Ci/mg. Cold yttrium (III) chloride was purchased from Sigma Aldrich. Beta radiation was quantified using a Beckman LS 6500 liquid scintillation counter. Samples were run for 20 minutes and an average value of two runs is given.

SPECIFIC EMBODIMENTS

1. A globular nanostructure having a hydrodynamic diameter ($D_h$) of 8-100 nm comprising a central part and a peripheral part, and wherein said central part has a calculated diameter ($D_c$) of 6-90 nm and said peripheral part has an estimated thickness ($T_p$) so that $D_h = D_c + 2T_p$ or $T_p = (D_h - D_c)/2$)

wherein said central part comprises:

(i) a crosslinked polymeric framework comprising monomer residues wherein at least 30% by number of the monomer residues have crosslinked thereby forming the crosslinked polymeric framework and/or (ii) a branched polymeric framework comprising monomer residues wherein the number of branch points is at least 30% of the number of monomer residues wherein said central part comprises chelating groups of which at least 4 allow chelation of at least one multiply charged cation, wherein said chelating groups are independently selected from the group consisting of —COOR$^1$, —P=O(OR$^1$)(OR$^2$), and —S(=O)$_2$OR$^1$, wherein R$^1$ and R$^2$ are independently selected from the group consisting of a negative charge, H, lower alkyls and aryl, and wherein said peripheral part comprises a synthetic polymer material covalently attached to the central part, wherein the synthetic polymer material is hydrophilic and bioinert, and electrically neutral or zwitterionic.

2. A globular nanostructure according to embodiment 1, wherein (i) a crosslinked polymeric framework comprising monomer residues wherein at least 50% by number of the monomer residues have crosslinked thereby forming the crosslinked polymeric framework and/or (ii) a branched polymeric framework comprising monomer residues wherein the number of branch points is at least 50% of the number of monomer residues.

3. A globular nanostructure according to embodiment 1 or 2, wherein R$^1$ and R$^2$ are independently a negative charge, H or methyl.

4. A globular nanostructure according to any one of the embodiments 1-3, having a hydrodynamic diameter of 8-50 nm.

5. A globular nanostructure according to any one of embodiments 1-4, having a hydrodynamic diameter of 8-20 nm.

6. A globular nanostructure according to any of the embodiments 1-5, wherein the hydrodynamic diameter, D$_h$ is 8-20 nm, the estimated diameter of the central part, D$_c$, is 6-15 nm and the thickness of the peripheral part is 1-2.5 nm.

7. A globular nanostructure according to any one of the embodiments 1-6, wherein said chelating groups comprise geminal bisphosphonate groups.

8. A globular nanostructure according to any one of the embodiments 1-7, wherein said chelating groups comprise geminal bisphosphonate groups which independently of each other are incorporated as

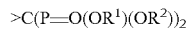

wherein:

R$^1$ and R$^2$ are independently selected from the group consisting of negative charge, H, lower alkyls, and aryl and >C denotes a carbon atom that is connected to or forms part of said crosslinked or branched polymeric framework.

9. A globular nanostructure according to any one of the embodiments 1-7, wherein said chelating groups comprises a multitude of phosphonate groups —P=O(OR$^1$)(OR$^2$) wherein R$^1$ and R$^2$ are independently selected from a negative charge, H, alkyl or aryl, with the proviso that when at least one of R$^1$ or R$^2$ is H the resulting phosphonic acid is ionized to a pH dependent extent.

10. A globular nanostructure according to any one of the embodiments 1-9, comprising phosphonates, wherein the phosphonates are a mixture of free phosphonates and the methyl esters of said phosphonate.

11. A globular nanostructure according to any one of the embodiments 1-10, wherein the crosslinked polymer framework is derived from polyethylene.

12. A globular nanostructure according to any one of the embodiments 1-10, wherein the crosslinked polymer framework is derived from polystyrene.

13. A globular nanostructure according to any one of the embodiments 1-10, wherein the crosslinked polymer framework is derived from polyacrylic acid.

14. A globular nanostructure according to any one of the embodiments 1-10, wherein the crosslinked polymer framework is derived from a hydrocarbon network.

15. A globular nanostructure according to embodiment 14, wherein the hydrocarbon network comprises crosslinked polyethylene.

16. A globular nanostructure according to embodiment 14, wherein the hydrocarbon network comprises crosslinked polystyrene.

17. A globular nanostructure according to any of the embodiments 1-16, wherein said central part comprises a homopolymer where there are 6 groups with potential for crosslinking in the monomer which corresponds to 600% of crosslinker added and 2-5 of them actually form crosslinks corresponding to 200-500% crosslinking achieved.

18. A globular nanostructure according to any of the embodiments 1-16 where the percentage of crosslinker added is 30-100%.

19. A globular nanostructure according to any of the embodiments 1-16 or 17, wherein the degree of crosslinking achieved is 30-100%.

20. A globular nanostructure according to any of the embodiments 1-16, wherein the degree of branching achieved is 30-100%.

21. A globular nanostructure according to any of the embodiments 1-16, wherein the degree of crosslinking achieved is 200-400%.

22. A globular nanostructure according to any of the embodiments 1-16, wherein the % of crosslinker added is 500-600%.

22. A globular nanostructure according to any of the embodiments 1-21, wherein the polymeric framework has been formed by condensation polymerization of trialkoxyorganosilanes R$^{12}$—Si(OR$^{13}$)$_3$, wherein R$^{12}$ is H or an organic residue and R$^{13}$ independently is a lower alkyl or aryl.

23. A globular nanostructure according to embodiment 22, wherein there are two alkoxysilane groups present in the monomer.

24. A globular nanostructure according to embodiment 23, wherein said alkoxysilanes are separated by 1-10 carbon atoms.

25. A globular nanostructure according to embodiment 23 or 24, wherein said alkoxysilanes are separated by 3-9 carbon atoms.

26. A globular nanostructure according to any of the embodiments 23-25, wherein said alkoxysilanes are separated by 7 carbon atoms.

27. A globular nanostructure according to any of the embodiments 23-26, wherein the two phosphonate groups are part of the R$^{12}$ group.

28. A globular nanostructure according to any of the embodiments 23-27, wherein said two alkoxysilanes are separated by 7 carbon atoms and the two phosphonate groups are part of the R$^{12}$ group.

29. A globular nanostructure according to any of the embodiments 23-28, wherein the monomers forming the polymeric framework have the generic structure:

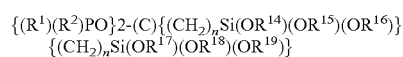

wherein
R¹ and R² are independently selected from the group consisting of negative charge, H, lower alkyls, and aryl and R$^{14}$, R$^{15}$, R$^{16}$, R$^{17}$, R$^{18}$, and R$^{19}$ are independently selected from the group consisting of lower alkyls and aryl; and
n=1-5.

30. A globular nanostructure according to any one of the embodiments 1-29, wherein said monomer residues include monomer residues having the structure

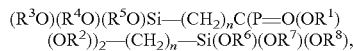
(OR²))₂—(CH₂)$_n$—Si(OR⁶)(OR⁷)(OR⁸), wherein R¹ and R² are independently selected from the group consisting of negative charge, H, lower alkyls, and aryl and R³, R⁴, R⁵, R⁶, R⁷, and R⁸ are independently selected from the group consisting of a negative charge, H, lower alkyls, and a bond to the polymeric network and n=1-5 such that the polymeric framework has been formed by means of —O—Si bonds, wherein the silicon atom is a silicon atom in the above structure.

31. A globular nanostructure according to embodiment 30, wherein R³, R⁴, R⁵, R⁶, R⁷, and R⁸ all are an ethyl group.

32. A globular nanostructure according to any one of the embodiments 29-31, wherein n=3.

33. A globular nanostructure according to any one of the embodiments 1-32, wherein the monomer residues forming the branched polymeric framework are independently selected from the group consisting of polyethyleneimine, modified polyethyleneimine, hyperbranched polyol, and hyperbranched triazine.

34. A globular nanostructure according to embodiment 33, wherein the monomer residues forming the branched polymeric framework are polyethyleneimine.

35. A globular nanostructure according to embodiment 35, wherein the polyethyleneimine has a degree of branching of 40-60%.

36. A globular nanostructure according to embodiment 34 or 35, wherein polyethyleneimine is adorned with chelating groups independently selected from the group consisting of —COOR¹, —P=O(OR¹)(OR²), and —S(=O)₂OR¹, wherein R¹ and R² are independently selected from the group consisting of a negative charge, H, lower alkyls, and aryl.

37 A globular nanostructure according to embodiments 34-36 wherein a number of negatively charged groups, such as carboxylates, can be introduced to make the whole nanostructure neutral at physiological pH.

38. A globular nanostructure according to any one of the embodiments 1-37, wherein said peripheral part comprises an electrically neutral synthetic polymer material.

39. A globular nanostructure according to any one of the embodiments 1-38, wherein said peripheral part comprises a synthetic polymer material selected from the group consisting of A-(O—CH₂CH₂)$_m$OR⁹, wherein m=2-100, R⁹ is a H or lower alkyls and A, m and R⁹ is a group that is linked to said polymeric framework, wherein A is selected from the group consisting of:
—OSiR¹⁰(CH₂)$_o$—, wherein R¹⁰ is selected from the group consisting of H or C₁-C₈ hydrocarbons and o=2-5;
—OSi(OR¹¹)₂(CH₂)$_o$—, wherein R¹¹ is selected from the group consisting of a covalent bond to the polymeric framework, H and C₁-C₈ hydrocarbons, and o=2-5;
—NR¹⁰—C=O—(CH₂)$_n$—, wherein R¹⁰ is as above and n=1-5
—O—C=O—(CH₂)$_n$—, wherein n=2-5;
—NR¹⁰—(CH₂)$_o$—, wherein R¹⁰ is as above and o=2-5;
—(CH₂)$_o$—, wherein o=2-5;
—O—(CH₂)$_o$—, wherein o=2-5; and
—SX₂—(CH₂)$_n$—, wherein X is independently nothing or O and n=1-5.

40. A globular nanostructure according to embodiment 39, wherein there are 0.5-2 A-(O—CH₂CH₂)$_n$OR⁹ groups attached per nm² of the interface between said central part and said peripheral part.

41. A globular nanostructure according to embodiment 39 or 40, wherein there are 0.5-2 μmol of said A-(O—CH₂CH₂)$_n$OR⁹ groups attached per m² of the interface between said central part and said peripheral part.

42. A globular nanostructure according to any one of the embodiments 39-41, wherein A-(O—CH₂CH₂)$_n$OR⁹ is covalently linked to the central part.

43. A globular nanostructure according to any one of the embodiments 1-37, wherein said peripheral part comprises a zwitterionic synthetic polymer material.

45. A globular nanostructure according to any of the embodiments 1-43, wherein the chelating groups comprises DOTA attached to the polymeric framework through an amide bond.

46. A globular nanostructure according to any of the embodiments 1-22 and 30, wherein said monomer residues include monomer residues having the structure (R²⁰)(R²¹)C(P=O(OR¹)(OR²))₂, wherein:
R¹ and R² are independently selected from the group consisting of negative charge, H, lower alkyls, and aryl;
R²⁰ is —(CH₂)$_n$CO— (with the carbonyl group forming the bond to the polymeric framework);
R²¹ is H or OH; and
n=1-5.

47. A globular nanostructure according to embodiment 46, wherein n=1.

48. A globular nanostructure according to embodiment 46 or 47, wherein R²⁰ and R²¹ independently are —(CH₂)$_n$—SiO₃, wherein n=1-5 and the silane is part of said polymeric framework by formation of Si—O—Si bonds.

49. A globular nanostructure according to embodiment 48, wherein R²⁰ and R²¹ independently are —(CH₂)$_n$—SiO₃, wherein n=3.

50. A globular nanostructure according to any one of the embodiments 1-49, wherein said peripheral part comprises a covalently attached linear, neutral, synthetic, bioinert, hydrophilic polymer.

51. A globular nanostructure according to any one of the embodiments 1-50, wherein the peripheral part comprises a covalently attached derivative of polyethyleneglycol.

52. A globular nanostructure according to embodiment 51, wherein the peripheral part comprises a covalently attached derivative of methyl terminated polyethyleneglycol.

53. A globular nanostructure according to embodiment 51 or 52, wherein the peripheral part comprises a covalently attached branched derivative of polyethyleneglycol.

54. A globular nanostructure according to embodiment 53, wherein the covalently attached branched derivative of polyethyleneglycol is:

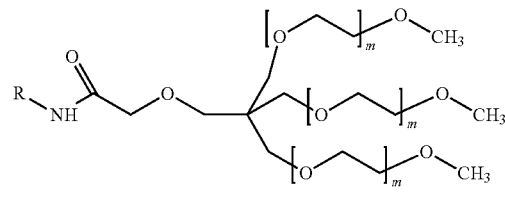

wherein R is said central part and m is independently 3-100.

55. A globular nanostructure according to any one of the embodiments 1-49, wherein the peripheral part comprises crosslinked polyacrylamide.

56. A globular nanostructure according to any one of the embodiments 1-49, wherein the peripheral part comprises dextran.

57. A composition comprising globular nanostructures according to any one of the embodiments 1-56, wherein the number average molecular weight is 50 000-300 000 000 Da, and the average hydrodynamic diameter of said nanostructures is above 8 nm.

58. A composition according to embodiment 57, wherein the average molecular weight is 50 000-50 000 000 Da.

59. A composition according to embodiment 57 or 58, wherein the average hydrodynamic diameter of said nanostructures is 8-100 nm.

60. A composition according to any one of the embodiments 57-59, wherein the average hydrodynamic diameter of said nanostructures is 8-50 nm.

61. A composition according to any one of the embodiments 57-60, wherein the average hydrodynamic diameter of said nanostructures is 8-20 nm.

62. A composition according to any one of the embodiments 57-61, wherein no more than 10% by number of the nanostructures are smaller than 8 nm.

63. A composition according to any one of the embodiments 57-62, wherein no more than 1% by number of the nanostructures are smaller than 8 nm.

64. A composition according to any one of the embodiments 57-63, wherein no more than 0.1% by number of the nanostructures are smaller than 8 nm.

65. A composition according to any one of the embodiments 57-64, wherein no more than 10% by weight of the nanostructures is excreted in the urine of a mammal within 24 hours of said mammal being intravenously injected with said composition.

66. A composition according to any one of the embodiments 57-65, wherein no more than 1% by weight of the nanostructures is excreted in the urine of a mammal within 24 hours of said mammal being intravenously injected with said composition.

67. A composition according to any one of the embodiments 57-66, wherein no more than 0.1% by weight of the nanostructures is excreted in the urine of a mammal within 24 hours of said mammal being intravenously injected with said composition.

68. A composition according to any one of the embodiments 57-67, wherein said mammal is a mouse, rat or human.

69. A composition according to any one of the embodiments 57-68, wherein said composition is a pharmaceutical composition which in addition to the nanostructures comprise a pharmaceutically acceptable carrier and/or adjuvant.

70. A composition according to any one of the embodiments 57-69 further comprising at least one radionuclide chelated to said nanostructures.

71. A composition according to embodiment 70, wherein the average number ratio (bound radionuclide):nanostructure is 0.1-20 000/nanostructure, with the proviso that the central part comprises at least 4 chelating groups available for each radionuclide.

72. A composition according to embodiment 70 or 71, wherein said radionuclide comprises a radionuclide for imaging and/or radiotherapy.

73. A composition according to embodiment 72, wherein said radionuclide for imaging and/or radiotherapy is selected from the group consisting of actinium-225 ($^{225}$Ac), copper-62 ($^{62}$Cu), copper-64 ($^{64}$Cu), copper-67 ($^{67}$Cu), gallium-67 ($^{67}$Ga), gallium-68 ($^{68}$Ga), holmium-166 ($^{166}$Ho), indium-111 ($^{111}$In), lead-212 ($^{212}$Pb), lutetium-177 ($^{177}$Lu), radium-223 ($^{223}$Ra), rhenium-186 ($^{186}$Re), rhenium-188 ($^{188}$Re), rubidium-82 ($^{82}$Rb), samarium-153 ($^{153}$Sm), strontium-89 ($^{89}$Sr), technetium-99m ($^{99m}$Tc$^{3+}$), thallium-201 ($^{201}$Tl), thorium-227 ($^{227}$Th), yttrium-86 ($^{86}$Y), yttrium-90 ($^{90}$Y), and zirconium-89 ($^{89}$Zr).

74. A composition according to embodiment 72 or 73, wherein said radionuclide comprises a radionuclide for imaging.

75. A composition according to embodiment 74, wherein said radionuclide comprises a radionuclide for PET imaging.

76. A composition according to embodiment 75, wherein said radionuclide for PET imaging is gallium-68 ($^{68}$Ga).

77. A composition according to embodiment 74, wherein said radionuclide comprises a radionuclide for SPECT imaging.

78. A composition according to embodiment 77, wherein said radionuclide for SPECT imaging is technetium-99m in its tri-cationic form ($^{99m}$Tc$^{3+}$).

79. A composition according to any one of the embodiments 72-78, wherein said radionuclide comprises a radionuclide for radiotherapy.

80. A composition according to embodiment 79, wherein said radionuclide for radiotherapy is yttrium-90 ($^{90}$Y).

81. A composition according to embodiment 72 or 73, wherein said radionuclide for imaging and/or radiotherapy is lutetium-177 ($^{177}$Lu).

82. A composition according to any one of the embodiments 70-81, when dependent on claim 69, wherein the pharmaceutical composition is formulated for parenteral injection.

83. A composition according to any one of the embodiments 70-81, when dependent on claim 69, wherein the pharmaceutical composition is formulated for intravenous injection.

84. A composition according to any one of the embodiments 70-81, when dependent on claim 69, wherein the pharmaceutical composition is formulated for rectal administration.

85. A composition according to any one of the embodiments 70-84 for use in a method of diagnosing and/or treating a soft tissue tumor.

86. A composition according to any one of the embodiments 70-84 for use in a method of diagnosing and/or treating a metastatic disease.

87. Use of a composition according to any one of the embodiments 70-84 for the production of a pharmaceutical composition for diagnosis and/or treatment of a soft tissue tumor.

88. Use of a composition according to any one of the embodiments 70-84 for the production of a pharmaceutical composition for diagnosis and/or treatment of a metastatic disease.

89. Use of a globular nanostructure according to any one of the embodiments 1-56 and a radionuclide for the production of a pharmaceutical composition for diagnosis and/or treatment of a soft tissue tumor.

90. Use of a composition according to any one of the embodiments 1-56 and a radionuclide for the production of a pharmaceutical composition for diagnosis and/or treatment of a metastatic disease.

91. Use according to embodiment 88 or 90, wherein said radionuclide comprises a radionuclide for imaging and/or radiotherapy.

92. Use according to any one of the embodiments 89-91, wherein said radionuclide is selected from the group consisting of actinium-225 ($^{225}$Ac), copper-62 ($^{62}$Cu), copper-64 (64Cu), copper-67 ($^{67}$Cu), gallium-67 ($^{67}$Ga), gallium-68 ($^{68}$Ga), holmium-166 ($^{166}$Ho), indium-111 ($^{111}$In), lead-212 ($^{212}$Pb), lutetium-177 ($^{177}$Lu), radium-223 ($^{223}$Ra), rhenium-186 ($^{186}$Re), rhenium-188 ($^{188}$Re), rubidium-82 ($^{82}$Rb), samarium-153 ($^{153}$Sm), strontium-89 ($^{89}$Sr), technetium-99m ($^{99m}$Tc$^{3+}$), thallium-201 ($^{201}$Tl), thorium-227 ($^{227}$Th), yttrium-86 ($^{86}$Y), yttrium-90 ($^{90}$Y), and zirconium-89 ($^{89}$Zr).

93. A method of treating a tumor and/or a metastatic disease in a patient in need of such treatment, comprising administering a therapeutically effective amount of globular nanostructure according to any one of the embodiments 1-56 and a radionuclide to the patient.

94. The method of embodiment 93, wherein said radionuclide is a radionuclide for imaging and/or radiotherapy.

95. The method of embodiment 94, wherein said radionuclide is selected from the group consisting of actinium-225 ($^{225}$Ac), copper-62 ($^{62}$Cu), copper-64 ($^{64}$Cu), copper-67 ($^{67}$Cu), gallium-67 ($^{67}$Ga), gallium-68 ($^{68}$Ga), holmium-166 ($^{166}$Ho), indium-111 ($^{111}$In), lead-212 ($^{212}$Pb), lutetium-177 ($^{177}$Lu), radium-223 ($^{223}$Ra), rhenium-186 ($^{186}$Re), rhenium-188 ($^{188}$Re), rubidium-82 ($^{82}$Rb), samarium-153 ($^{153}$Sm), strontium-89 ($^{89}$Sr), technetium-99m ($^{99m}$Tc$^{3+}$), thallium-201 ($^{201}$Tl), thorium-227 ($^{227}$Th), yttrium-86 ($^{86}$Y), yttrium-90 ($^{90}$Y), and zirconium-89 ($^{89}$Zr).

96. A method of treating a tumor in a patient in need of such treatment, comprising administering a therapeutically effective amount of composition according to any one of the embodiments 70-84.

97. The method of any one of the embodiments 93-96, wherein said tumor is a soft tissue tumor.

98. A method of diagnosing the presence of a tumor in a subject, comprising administering a diagnostically effective amount of globular nanostructure according to any one of the embodiments 1-56 and a radionuclide to the patient.

990. The method of embodiment 98, wherein said radionuclide is a radionuclide for imaging and/or radiotherapy.

100. The method of embodiment 99, wherein said radionuclide is selected from the group consisting of actinium-225 ($^{225}$Ac), copper-62 ($^{62}$Cu), copper-64 ($^{64}$Cu), copper-67 ($^{67}$Cu), gallium-67 ($^{67}$Ga), gallium-68 ($^{68}$Ga), holmium-166 ($^{166}$Ho), indium-111 ($^{111}$In), lead-212 ($^{212}$Pb), lutetium-177 ($^{177}$Lu), radium-223 ($^{223}$Ra), rhenium-186 ($^{186}$Re), rhenium-188 ($^{188}$Re), rubidium-82 ($^{82}$Rb), samarium-153 ($^{153}$Sm), strontium-89 ($^{89}$Sr), technetium-99m ($^{99m}$Tc$^{3+}$), thallium-201 ($^{201}$Tl), thorium-227 ($^{227}$Th), yttrium-86 ($^{86}$Y), yttrium-90 ($^{90}$Y), and zirconium-89 ($^{89}$Zr).

101. A method of diagnosing the presence of a tumor in a subject, comprising administering a diagnostically effective amount of composition according to any one of the embodiments 70-84.

102. The method of any one of the embodiments 98-101, wherein said tumor is a soft tissue tumor.

103. A method of obtaining a composition according to any one of the embodiments 70-86, comprising contacting the nanostructures according to any one of the claims 1-56, with at least one radionuclide.

104. A kit for preparing a composition according to any one of the embodiments 57-69, comprising a plurality of nanostructures according to claims 1-56 dissolved in an aqueous buffer with a pH of 6-7.5 and an osmolality of 500-2000 mOsm/kg.

105. A kit for preparing a composition according to any one of the embodiments 70-86, comprising a plurality of nanostructures according to claims 1-56 dissolved in an aqueous buffer with a pH of 6-7.5 and an osmolality of 500-2000 mOsm/kg, and a radionuclide.

106. A kit according to embodiment 105, wherein the radionuclide is present in cationic form in a solution.

107. A kit according to any one of the embodiments 104-106, wherein the aqueous buffer comprises a pH regulator.

108. A kit according to embodiment 107, wherein the pH regulator is selected from the group consisting of acetate, bicarbonate, lactate, citrate, malate and propionate.

109. A kit according to any one of the embodiments 104-108, further comprising an osmoregulator.

110. A kit according to embodiment 109, wherein the osmoregulator is selected from the group consisting of sodium chloride, mannitol, sorbitol, calcium chloride, magnesium chloride, and glycerol.

111. A globular nanostructure produced by a process comprising the steps of:
1) forming a central part by a hydrolytic polymerization of a disilane of the structure

wherein
$R^1$ and $R^2$ are independently selected from the group consisting of negative charge, H, lower alkyls, and aryl and $R^{14}$, $R^{15}$, $R^1$, $R^{17}$, $R^{18}$, and $R^{19}$ are independently selected from the group consisting of lower alkyls and aryl;
and
n=1-5; and
2) contacting said central part with a precursor of the peripheral part under conditions conducive to said part covalently linking to said central part.

The invention claimed is:

1. A globular nanostructure having a hydrodynamic diameter ($D_h$) of 8-100 nm comprising a central part and a peripheral part, wherein said central part has a calculated diameter ($D_c$) of 6-90 nm and said peripheral part has an estimated thickness ($T_p$) so that $D_h=D_c+2T_p$,
wherein said central part comprises:
(i) a crosslinked polymeric framework comprising monomer residues wherein at least 30% by number of the monomer residues have crosslinked thereby forming the crosslinked polymeric framework and/or
(ii) a branched polymeric framework comprising monomer residues wherein the number of branch points is at least 30% of the number of monomer residues,
wherein said central part comprises chelating groups of which at least 4 allow chelation of at least one multiply charged cation, wherein said chelating groups are independently selected from the group consisting of —COOR$^1$, —P—O(OR$^1$)(OR$^2$), and —S(=O)$_2$OR$^1$, wherein R$^1$ and R$^2$ are independently selected from the group consisting of a negative charge H, lower alkyls, aryl,
wherein said peripheral part comprises a synthetic polymer material covalently attached to the central part, wherein the synthetic polymer material is hydrophilic and bioinert, and electrically neutral or zwitterionic,
wherein said peripheral part comprises a synthetic polymer material selected from the group consisting of A-(O—CH$_2$CH$_2$)$_m$OR$^9$, wherein m=2-100, R$^9$ is a H or lower alkyls and A is a group that is linked to said polymeric framework, wherein A is selected from the group consisting of:

—OSi(R$^{10}$)$_2$(CH$_2$)$_o$—, wherein R$^{10}$ is selected from the group consisting of C$_1$-C$_8$ hydrocarbons and o=2-5;

—OSi(OR$^{11a}$)(OR$^{11b}$)(CH$_2$)$_o$—, wherein R$^{11a}$ and R$^{11b}$ are the same or different and each is independently selected front the group consisting of a covalent bond to the polymeric framework, H and C$_1$-C$_8$ hydrocarbons and o=2-5;

—NR$^{10}$—C=O—(CH$_2$)$_n$—, wherein R$^{10}$ is as above and n=1-5

—O—C=O—(CH$_2$)$_n$—, wherein n=1-5;

—NR$^{10}$—(CH$_2$)$_o$, wherein R$^{10}$ is as above and o=2-5;

—(CH$_2$)$_o$—, wherein o=2-5;

—O—(CH$_2$)$_o$—, wherein o=2-5; and

—SX$_2$—(CH$_2$)$_n$—, wherein X is independently nothing or O and n≤1-5, and wherein there are 0.5-2 A-(O—CH$_2$CH$_2$)$_m$OR$^9$ groups attached per nm$^2$ of the interface between said central part and said peripheral part, and further comprising a radionuclide chelated to said nanostructure.

2. A nanostructure according to claim 1, wherein said chelating groups comprise geminal bisphosphonate groups which independently of each other are incorporated as

wherein:

R$^1$ and R$^2$ are independently selected from the group consisting of negative charge, H, lower alkyls, and aryl and >C denotes a carbon atom that is connected to or forms part of said crosslinked or branched polymeric framework.

3. A nanostructure according to claim 1, wherein said monomer residues include monomer residues having the structure (R$^3$O)(R$^4$O)(R$^5$O)Si—(CH$_2$)$_n$C(P=O(OR$^1$)(OR$^2$))$_2$—(CH$_2$)$_n$—Si(OR$^6$)(OR$^7$)(OR$^8$), wherein R$^1$ and R$^2$ are as defined above and R$^3$, R$^4$, R$^5$, R$^6$, R$^7$, and R$^8$ are independently selected from the group consisting of a negative charge, H and lower alkyls, or a bond to the polymeric framework and n=1-5 such that the polymeric framework has been formed by means of —O—Si bonds, wherein the silicon atom is a silicon atom in the above structure.

4. A nanostructure according to claim 1, wherein the branched polymeric framework is independently selected from the group consisting of polyethyleneimine, modified polyethyleneimine, hyperbranched polyol, and hyperbranched triazine.

5. A nanostructure according to claim 1, wherein the branched polymeric framework of the central part is polyethyleneimine and the peripheral part comprises —NH(C=O)(CH$_2$)$_n$—(O—CH$_2$CH$_2$)$_m$OR$^9$, wherein n=1-5, m=2-100, R$^9$ is a H or lower alkyls; and the chelating groups comprise 1,4,7,10-tetraazacyclododecane-1,4,7,10-tetraacetic acid residues.

6. A nanostructure according to claim 1, wherein the radionuclide(s) chelated to the nanostructures comprises $^{90}$Y.

7. A nanostructure according to claim 1, wherein the radionuclide(s) chelated to the nanostructures comprises $^{99m}$Tc$^{3+}$.

8. A nanostructure according to claim 1, wherein the radionuclide(s) chelated to the nanostructures comprises $^{177}$Lu.

9. A composition comprising nanostructures according to claim 1, wherein the number average molecular weight is 50 000-300 000 000 Da and the average hydrodynamic diameter of said nanostructures is 8-100 nm.

10. A composition according to claim 9, wherein no more than 10% by number of the nanostructures are smaller than 8 nm.

11. A composition according to claim 9, wherein the average number ratio (bound radionuclide):nanostructure is 0.1-20 000, with the proviso that the central part of the nanostructure comprises at least 4 chelating groups available for each radionuclide.

12. A method for imaging and/or radiotherapy in a subject in need thereof, the method comprising administering the composition according to claim 9 to the subject.

13. A kit for preparing a composition according to claim 9, comprising a multitude of nanostructures dissolved in an aqueous buffer with a pH of 6-7.5 and an osmolality of 500-2000 mOsm/kg.

* * * * *